US010716878B2

(12) United States Patent
Soo et al.

(10) Patent No.: US 10,716,878 B2
(45) Date of Patent: Jul. 21, 2020

(54) NANOPARTICLE-BASED SCAFFOLDS AND IMPLANTS, METHODS FOR MAKING THE SAME, AND APPLICATIONS THEREOF

(71) Applicant: The Regents of the University of California, Oakland, CA (US)

(72) Inventors: B. Chia Soo, Beverly Hills, CA (US); Kang Ting, Beverly Hills, CA (US); Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/353,286

(22) PCT Filed: Oct. 19, 2012

(86) PCT No.: PCT/US2012/061217
§ 371 (c)(1),
(2) Date: Apr. 21, 2014

(87) PCT Pub. No.: WO2013/059745
PCT Pub. Date: Apr. 25, 2013

(65) Prior Publication Data
US 2014/0287018 A1    Sep. 25, 2014

Related U.S. Application Data

(60) Provisional application No. 61/550,349, filed on Oct. 21, 2011.

(51) Int. Cl.
| | |
|---|---|
| *A61L 27/34* | (2006.01) |
| *A61L 31/16* | (2006.01) |
| *A61L 31/06* | (2006.01) |
| *A61L 27/54* | (2006.01) |
| *A61C 8/00* | (2006.01) |
| *A61L 31/10* | (2006.01) |
| *A61F 2/30* | (2006.01) |
| *A61F 2/44* | (2006.01) |

(52) U.S. Cl.
CPC ............ *A61L 31/06* (2013.01); *A61C 8/0016* (2013.01); *A61L 27/34* (2013.01); *A61L 27/54* (2013.01); *A61L 31/10* (2013.01); *A61L 31/16* (2013.01); *A61F 2/4455* (2013.01); *A61F 2002/3084* (2013.01); *A61F 2310/0052* (2013.01); *A61F 2310/0097* (2013.01); *A61F 2310/00359* (2013.01); *A61F 2310/00365* (2013.01); *A61F 2310/00976* (2013.01); *A61L 2300/104* (2013.01); *A61L 2300/404* (2013.01); *A61L 2400/12* (2013.01)

(58) Field of Classification Search
CPC .......... A61L 31/06; A61L 31/16; A61L 27/51; A61L 31/10; A61L 27/34; A61L 2400/12; A61L 2300/104; A61L 2300/404; A61C 8/0016; A61F 2310/00365; A61F 2310/0052; A61F 2310/00976; A61F 2310/0097; A61F 2/4455; A61F 2002/3084; A61F 2310/00359

See application file for complete search history.

(56) References Cited

U.S. PATENT DOCUMENTS

| | | | | |
|---|---|---|---|---|
| 2007/0282247 | A1* | 12/2007 | Desai | ................. A61L 27/54 604/19 |
| 2007/0299518 | A1* | 12/2007 | Ruane | ................. A61L 27/34 623/11.11 |
| 2008/0050509 | A1 | 2/2008 | Nesbitt | |
| 2008/0249638 | A1* | 10/2008 | Asgari | ................. A61F 2/28 623/23.75 |
| 2010/0331613 | A1* | 12/2010 | Centonze | ............ A61L 27/446 600/37 |
| 2011/0008407 | A1 | 1/2011 | Gan et al. | |

FOREIGN PATENT DOCUMENTS

WO     2013059745 A1    4/2013

OTHER PUBLICATIONS

Brace "Amides as Nucleophiles: Reaction of alkyl halides with amides or with amides and water. A new look at an old reaction", J Org Chem 56: 1804-1811 (1993).*
International Search Report for International Application No. PCT/US2012/061217, dated Mar. 29, 2013.
Written Opinion of the International Searching Authority for International Application No. PCT/US2012/061217, dated Mar. 29, 2013.
International Preliminary Report on Patentability International Application No. PCT/US2012/061217, dated Apr. 22, 2014.
Soo, B., Chia; International Preliminary Report on Patentability for serial No. PCT/US2012/061217, filed Oct. 19, 2012, dated May 1, 2014, 7 pgs.

* cited by examiner

*Primary Examiner* — Mina Haghighatian
(74) *Attorney, Agent, or Firm* — Taylor English Duma LLP

(57) ABSTRACT

Implant-associated bacterial infections are one of the most serious complications in orthopedic surgery. Treatment of these infections often requires multiple operations, device removal, long-term systemic antibiotics, and extended rehabilitation, and is frequently ineffective, leading to worse clinical outcomes and increased financial costs. Silver nanoparticle/poly(DL-lactic-co-glycolic acid) (PLGA)-coated stainless steel alloy (SNPSA) was evaluated as a potential antimicrobial implant material. It was found that SNPSA exhibited strong antibacterial activity in vitro and ex vivo, and promoted MC3T3-E1 pre-osteoblasts proliferation and maturation in vitro. Furthermore, SNPSA implants induced osteogenesis while suppressing bacterial survival in contaminated rat femoral canals. The results indicate that SNPSA has simultaneous antimicrobial and osteoinductive properties that make it a promising therapeutic material in orthopedic surgery.

21 Claims, 17 Drawing Sheets

6A

6B

6C

7A

7B

7C

13A

13B

NANOPARTICLE-BASED SCAFFOLDS AND IMPLANTS, METHODS FOR MAKING THE SAME, AND APPLICATIONS THEREOF

CROSS-REFERENCE TO RELATED APPLICATIONS

This application claims priority to International Application No. PCT/US2012/061217, filed on Oct. 19, 2012, which in turn claims priority from U.S. Provisional Patent Application No. 61/550,349, filed on Oct. 21, 2011, each of which is incorporated herein by reference in its entirety.

STATEMENT REGARDING FEDERALLY-SPONSORED RESEARCH

This invention was made with Government support of Grant No. W81XWH-09-1-0090, awarded by the United States Army Medical Research and Materiel Command. The Government has certain rights in the invention.

FIELD OF THE INVENTION

The invention disclosed herein generally relates to devices (e.g., scaffolds, fixture and/or implants) for osteoconductive applications. In particular, the invention relates to nanoparticle-based scaffolds and/or implants and methods for making the same. The invention further relates to applications of these devices.

BACKGROUND

Implant-associated microbial infections are one of the most serious complications in orthopedic surgery because they are extremely difficult to treat and result in increased morbidity and substantially worse outcomes. Despite a recent focus on aseptic surgical and procedural techniques, catheter- and surgical implant-associated infections account for nearly half of the 2 million cases of nosocomial infections in the United States per year, representing a significant healthcare and economic burden. Devices and methods for imaging sub-millimeter-sized tumors that are embedded in tissues (e.g., at depths greater than 1-2 mm) are not available. Consequently, methods for treating such tumors are also lacking due to the inability in combining high specific and sensitive imaging with highly conformal radiation.'

Management of an implant-associated infection typically requires device removal, multiple debridement surgeries, and long-term systemic antibiotic therapy, despite the associated side effects and additional complications. However, these additional surgical procedures and medical therapies not only increase the healthcare costs, but also result in an increased rate of recurrence, particularly because it is difficult to clear the infection from devascularized bone and other necrotic tissues. Soon after introduction of an implant, a conditioning layer composed of host-derived adhesins (including fibrinogen, fibronectin, collagen, etc.) covers the surface of the implant. This layer promotes adherence of free-floating (planktonic) bacteria, which subsequently form an extracellular anionic polysaccharide 3 dimensional (3D) biofilm. Once a biofilm forms, it is extremely difficult to treat these infections because the biofilm blocks the penetration of both host immune cells (such as macrophages) and systemic antibiotics, promoting further bacterial survival. Given the difficulties in treating implant-associated infections, strategies aimed at preventing the infection and biofilm formation during surgery and in the immediate postoperative period may serve as more effective alternative that can prevent these infections altogether.

Prior studies have coated or covalently-linked antibiotics onto prosthetic materials to prevent bacterial infection during surgical implantation. Although this local antibiotic therapy may be effective, they are limited to certain bacterial species and these infections can be caused by a spectrum of bacteria, including Gram-positive *Staphylococcus aureus, Staphylococcus epidermidis* and *Streptococci* species, and Gram-negative *Pseudomonas* and *Enterobacter* species. Moreover, antibiotics used in this manner can contribute to the development of antibiotic resistance, which is especially relevant as there is an increasing number of infections caused by methicillin-resistant *S. aureus* (MRSA) and methicillin-resistant *S. epidermidis* (MRSE) strains.

What is needed in the art are implant materials or coatings that can resist infection while simultaneously promoting bone growth. Such materials and/or devices made therefrom would be particularly advantageous for orthopedic surgery applications.

SUMMARY OF THE INVENTION

Provided herein are medical devices that can reduce or eliminate microbial infections. In some embodiments, the devices are implantable devices that comprise a plurality of silver nanoparticles dispersed in a polymeric material.

In some embodiments, the silver nanoparticles are deposited in an antimicrobial polymeric coating on at least a portion of a surface of the implantable device.

In some embodiments, the silver nanoparticles are embedded in a substrate forming the implantable device.

In some embodiments, an implantable device is selected from the group consisting of an implantable intervertebral device, a cervical fusion device, a scaffold, a fixture, a dental implant, a dental disc, a dental bridge, a retainer clip, a dental screw, a dental housing, a dental bone graft, a dental crown, an orthopedic implant, an intramedullary rod, a temporary pin, a permanent pin, a bone plate, a bone screw, and a combination thereof.

In some embodiments, the polymeric material is selected from the group consisting of a biocompatible polymer, a biodegradable polymer, a bioabsorbable polymer, and a combination thereof.

In some embodiments, the silver nanoparticles constitute about 5% or less by weight of the polymeric material.

In some embodiments, the silver nanoparticles constitute about 2% or less by weight of the polymeric material.

In some embodiments, the silver nanoparticles have a mean size of 100 nm or smaller.

In some embodiments, the silver nanoparticles have a mean size of 80 nm or smaller.

In some embodiments, the silver nanoparticles have a mean size of 50 nm or smaller.

In some embodiments, the silver nanoparticles have a mean size of 40 nm or smaller.

In some embodiments, the silver nanoparticles have a mean size of between 20 nm and 40 nm.

In some embodiments, the silver nanoparticles have a mean size of 30 nm or smaller.

In some embodiments, the silver nanoparticles have a mean size of 40 nm or smaller.

In some embodiments, an additional polymeric coating is deposited over the silver nanoparticles.

In some embodiments, the antimicrobial polymeric coating further comprises a therapeutic agent.

In some embodiments, the additional polymeric coating further comprises a therapeutic agent.

Also provided herein are methods of making the implantable devices. In some embodiments, a device can be rendered anti-microbial by depositing a coating on a surface of the device. The coating comprises an anti-microbial such as nanosilver, alone or in combination with another therapeutic or bioactive agent. In some embodiments, a device can constructed with material that itself has anti-microbial properties; for example, using a polymeric material comprising as nanosilver, alone or in combination with another therapeutic or bioactive agent.

Further provided herein are and methods for using the devices in reducing or eliminating microbial infections. For example, the devices can be used to eliminate or reduce a source of microbial infection that can be introduced during a surgical procedure when the device (e.g., a scaffold, a fixture or an implant) is introduced into a recipient (e.g., a mammal). In some embodiments, the source of microbial infection can be an additional bioactive agent that the device can be used to mask.

BRIEF DESCRIPTION OF THE DRAWINGS

Those of skill in the art will understand that the drawings, described below, are for illustrative purposes only. The drawings are not intended to limit the scope of the present teachings in any way.

on the silver proportion of various SNPSAs during the 9-day incubation in osteogenic medium in vitro. N=6; #, significant difference compared to 0%-SNPSA, ANOVA<0.05; *, significant difference between before and after incubation in osteogenic medium, P<0.05; error bars were too small to show.

FIGS. 4A through 4D an exemplary embodiment. In vitro protein adsorption of SNPSAs. Adsorption of the total serum protein (A), bovine serum albumin (BSA) (B), and bone morphogenetic protein (BMP)-2 (C) was measured after 0 and 9 hours of incubation in osteogenic medium. The ratio of protein adsorption of BMP-2/BSA is also shown (D). Data normalized to 0%-SNPSA on day 0. N=6; #, significant difference compared to 0%-SNPSA, ANOVA<0.05; *, significant difference before and after incubation in osteogenic medium, P<0.05; error bars were too small to show.

Figure 5:
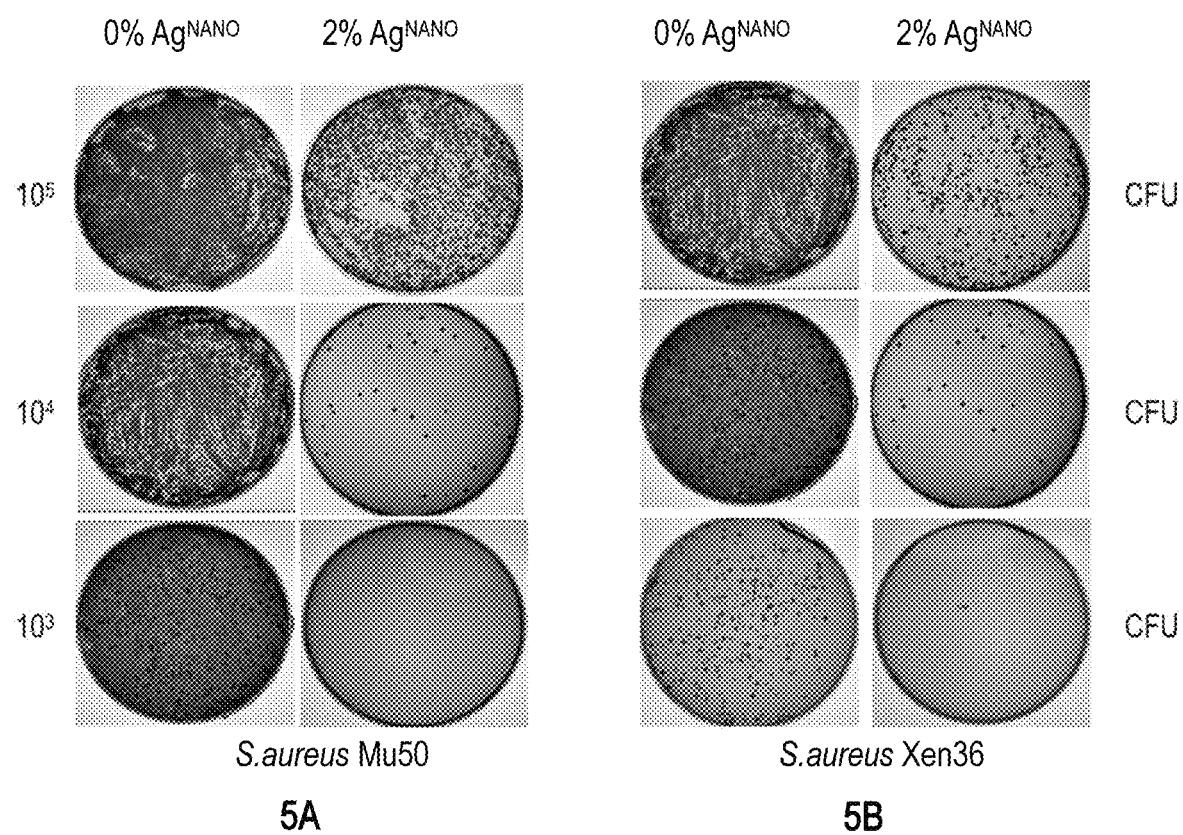

FIGS. 5A and 5B illustrate an exemplary embodiment. In vitro antibacterial activity of nanosilver coated K-wires (0% $Ag^{NANO}$ and 2% $Ag^{NANO}$). Different inocula [$10^3$, $10^4$ and $10^5$ colony formation unit (CFU)] of S. aureus Mu50 (A) and Xen36 (B) were incubated in 1 ml broth with nanosilver coated K-wires at 37° C. for 1 h to allow adherence of the microorganisms to the nanosilver coated K-wire surface. After rinsing with phosphate buffered saline (PBS), nanosilver coated K-wires were incubated in 1 ml PBS nutrient for 18 h at 37° C.; 100 µl of the PBS solution was then spread on agar plates for 20 h incubation. The antibacterial effect of nanosilver coated K-wires were evaluated with bacterial colony formation after overnight culture.

FIGS. 6A, 6B and 6C illustrate an exemplary embodiment. In vitro bacterial colonization analysis of S. aureus Mu50. Antimicrobial activity of SNPSA against $10^3$ (A), $10^4$ (B), and $10^5$ (C) CFU S. aureus Mu50 was evaluated. Bacteria were incubated in 1 ml broth with SNPSA K-wires at 37° C. to adherence. At the end of the incubation, bacteria attached to the surface were collected in sterile 0.9% saline solution by sonication for 30 s at 0.6 power with an intermediate size probe and plated onto 10-cm brain-heart infusion broth (BHIB) culture medium plates overnight. After 18 h incubation, the number of colonies on each plate was quantitated following protocols set forth by the U.S. Food and Drug Administration (FDA), for example, in their Bacteriological Analytical Manual and Aerobic Plate Count Method. (accessible at the FDA website, e.g., at www<dot>fda<dot>gov</>Food</>ScienceResearch</>LaboratoryMethods</>BacteriologicalA nalyticalManual-BAM</>ucm063346<dot>htm). SNPSA inhibited S. aureus Mu50 initial adherence and extended proliferation in a silver-proportion-dependent manner in vitro. N=4; *, significant difference compared to 0%-SNPSA, ANOVA<0.05; error bars were too small to show.

FIGS. 7A, 7B and 7C illustrate an exemplary embodiment. In vitro bacterial colonization analysis of P. aeruginosa PAO-1. Antimicrobial activity of SNPSAs against $10^3$ (A), $10^4$ (B), and $10^5$ (C) CFU P. aeruginosa PAO-1 was evaluated. Bacteria were incubated in 1 ml broth with SNPSA K-wires at 30° C. to adherence. At the end of the incubation, bacteria attached to the surface were collected in sterile 0.9% saline solution by sonication for 30 s at 0.6 power with an intermediate size probe and plated onto 10-cm LB culture medium plates overnight. After 18 h incubation, the number of colonies on each plate was quantitated following protocols set forth by the U.S. Food and Drug Administration (FDA), for example, in their Bacteriological Analytical Manual and Aerobic Plate Count Method (accessible at the FDA website, e.g., www<dot>fda<dot>gov</>Food</>ScienceResearch</>LaboratoryMethods</>BacteriologicalA nalyticalManual-BAM</>ucm063346<dot>htm). SNPSA inhibited P. aeruginosa PAO-1 initial adherence and extended proliferation in a silver-proportion-dependent manner in vitro. N=4; *, significant difference compared to 0%-SNPSA, ANOVA<0.05; error bars were too small to show.

FIGS. 8A through 8D illustrate an exemplary embodiment. Ex vivo antibacterial activity of nanosilver coated K-wires (0% $Ag^{NANO}$ and 2% $Ag^{NANO}$). Different inocula (A, C, $10^3$ CFU and B, D, $10^5$ CFU respectively) of S. aureus Mu50 (A, B) and Xen36 (C, D) were tested with ex vivo model for 18 h incubation at 37° C. After rinsing with PBS, nanosilver coated K-wires were incubated in 1 ml PBS nutrient for another 18 h at 37° C.; 100 μl of the PBS solution was then amplified by adding 100 μl fresh broth for a 40 h-kinetics test with microplate proliferation assay.

FIGS. 9A through 9F illustrate an exemplary embodiment. Ex vivo antimicrobial activity of SNPSAs. Using an ex vivo antimicrobial model, antimicrobial activity of SNPSAs against $10^3$ (A), $10^4$ (B), and $10^5$ (C) CFU S. aureus Mu50, as well as $10^3$ (D), $10^4$ (E), and $10^5$ (F) CFU P. aeruginosa PAO-1, was evaluated ex vivo. SNPSA effectively inhibited bacterial proliferation in a silver-proportion-dependent manner. N=3; *, significant difference compared to 0%-SNPSA, ANOVA<0.05.

FIGS. 10A through 10F illustrate an exemplary embodiment. Creation of ex vivo model for nanosilver coated K-wires. (A) Isolated mouse femur. (B) Coated K-wires (upper: 0% nanosilver, lower: 2% nanosilver, length: 1 cm). (C) An intramedullary canal was manually reamed into the distal femur with a 25 gauge needle (arrow). (D) An orthopaedic-grade stainless steel nanosilver coated Kirschner wire was then placed in the intramedullary canal (arrow). (E) An inocula of S. aureus Mu50 or Xen36 in a 2 μl volume was then pipetted into the intramedullary canal and was attached on the nanosilver coated K-wires (arrow). (F) Isolated mouse femur with nanosilver coated K-wire and pipetted with $10^3$ or $10^5$ CFU S. aureus Mu50 or Xen36. Scale bar: 5 mm.

Figure 11:
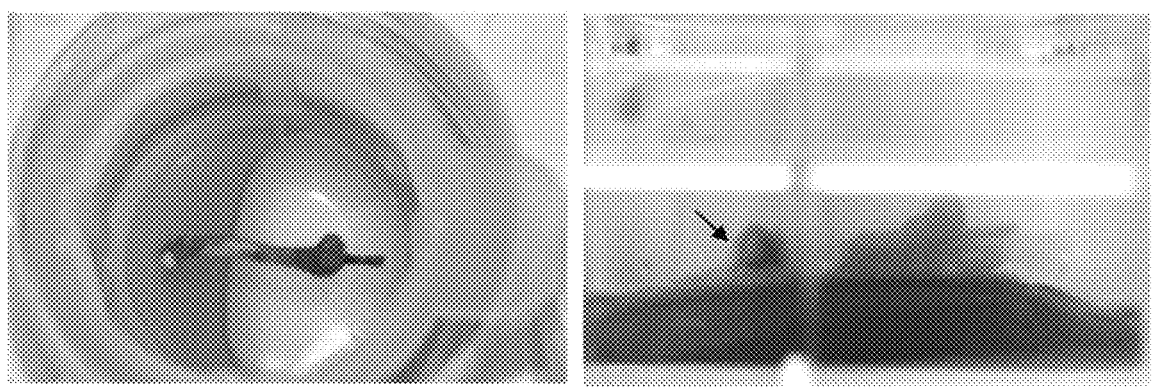

FIGS. 11A and 11B an exemplary embodiment. Ex vivo culture model for nanosilver coated K-wires. (A) Top view of isolated mouse femur with nanosilver coated K-wire injected with 2 μl containing $10^3$ or $10^5$ CFU S. aureus Mu50 or Xen36 and incubated in 100 μm cell strainers within 6-well cell culture plates. (B) Lateral view of incubation model. The distal femur with the protruding K-wire is angled superiorly so that the proximal femur is in contact with culture medium, while the nanosilver coated K-wire does not directly contact the culture medium.

FIGS. 12A through 12F illustrate an exemplary embodiment. Ex vivo antimicrobial model. Femurs isolated from 12-week old male 129/sv mice (A) were used for SNPSA ex vivo antimicrobial activity test. After locating the femoral intercondylar notch, an intramedullary canal was manually reamed into the distal femur with a 25-gauge needle (B). A SNPSA K-wire was then placed into the intramedullary canal (C) with 2 μl bacteria suspended in PBS (D). These femurs with implants (E) were placed on a 100 μm cell strainer within 6-well cell culture plate containing 2 ml medium (F). In order to avoid direct contact between SNPSA and cell culture medium, the distal femur with a protruding SNPSA was angled superiorly, and the proximal femur was soaked in culture medium.

Figure 13:
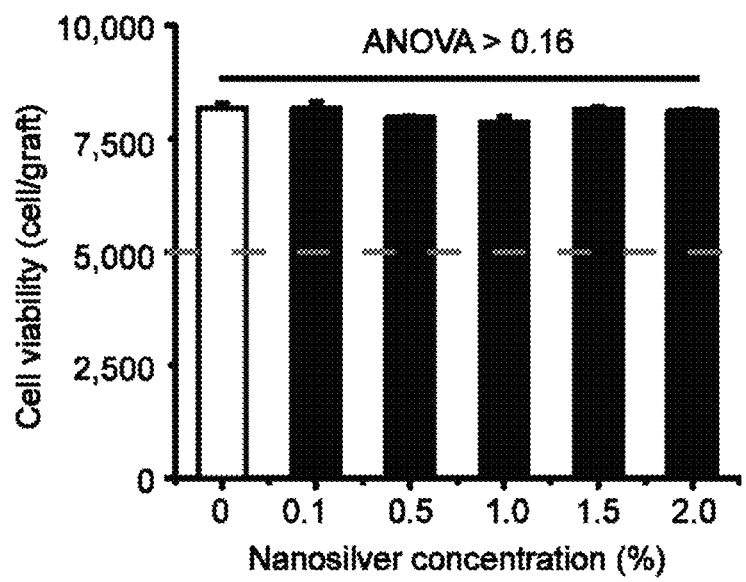
Figure 13:
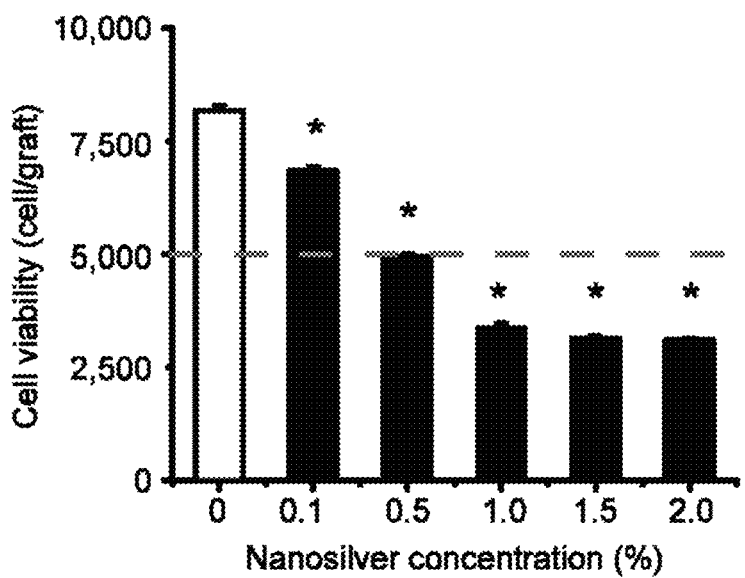

FIGS. 13A and 13B illustrate an exemplary embodiment, demonstrating selective inhibition of fibroblast proliferation over osteoblast proliferation. (A) 5,000 pre-osteoblastic MC3T3-E1 (subclone 4, ATCC CRL-2593) cells were seeded on nanosilver/PLGA composite (NS/PLGA) grafts (red line). After cultured in α-minimal essential medium (α-MEM) supplied with 10% fetal bovine serum (FBS), 1% HT supplement, and 1% penicillin/streptomycin for 4 days at 37° C. with 5% CO, cell viability was evaluated by Vybrand® MTT Cell Proliferation Assay Kit. Up to 2.0% nanosilver affected the viability of MC3T3-E1 cells proliferation. (B) 5,000 rat dermal fibroblast Rat2 (ATCC CRL-1764) cells were seeded on nanosilver/PLGA composite (NS/PLGA) grafts (red line). After cultured in Dulbecco's Modified Eagle Medium (DMEM) supplied with 10% FBS, and 1% penicillin/streptomycin for 4 days at 37° C. with 5% CO2, cell viability was evaluated by Vybrand® MTT Cell Proliferation Assay Kit. Nanosilver showed obvious cytotoxicity to fibroblasts. Data were descripted as mean±standard error of mean. N=6; *, P<0.001.

Figure 14:
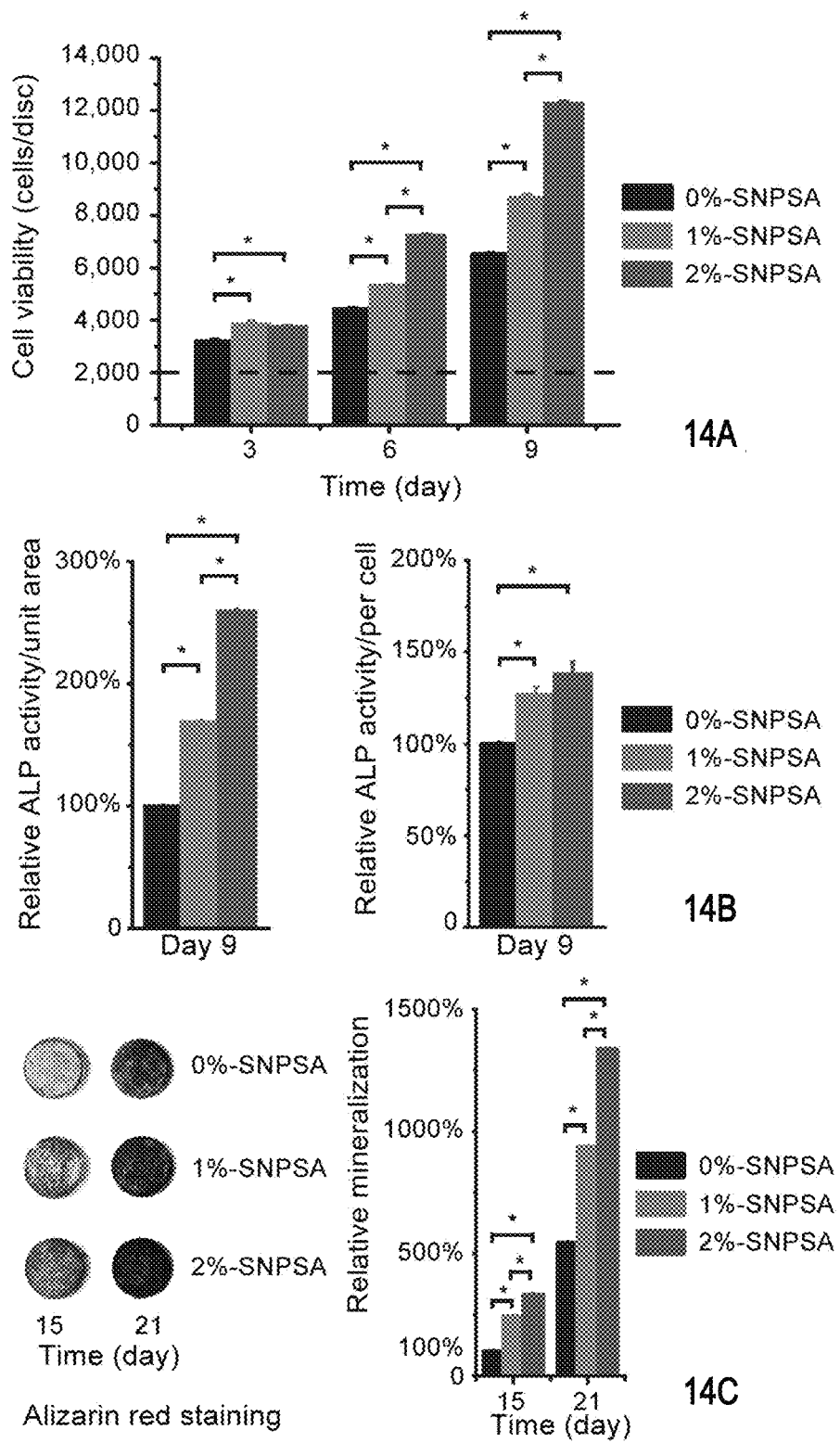

FIGS. 14A, 14B, and 14C illustrate an exemplary embodiment. In vitro osteoinductive activity of SNPSAs. $2 \times 10^3$ pre-osteoblastic MC3T3-E1 murine cells (passage 18, subclone 4, ATCC CRL-2593) were seeded on SNPSA discs with 500 ml osteogenic medium (α-MEM supplied with 10% FBS, 1% HT supplement, 1% penicillin/streptomycin, 50 μg/ml ascorbic acid and 10 mM β-glycerophosphate) in 24-well plates at 37° C., 5% CO2, and 95% humidity. All media for cell culture were purchased from Invitrogen. Cell proliferation was estimated using the Vybrand® MTT Cell Proliferation Assay Kit (Invitrogen). Alkaline phosphatase (ALP) activity and degree of mineralization (assessed by Alizarin Red staining) were used to quantify the effect of SNAPS on osteoblastic differentiation. SNPSAs significantly promoted MC3T3-E1 cell proliferation (A), ALP activity (B), and mineralization (C). Data normalized to 0%-SNPSA on day 9 (b) and on day 15 (c). N=6; *, P<0.05.

FIGS. 15A and 15B illustrate exemplary radiographic images of uncontaminated 0%- and 2%-SNPSA implants in rat femoral canals (FCs). All surgical procedures were approved by the UCLA Office of Animal Research Oversight (protocol #2008-073). Using aseptic technique, a 25-30 mm longitudinal incision was made over the anterolateral aspect of the left femur of 12-week old male Sprague-Dawley (SD) rats. The femoral shaft was then exposed by separating the vastus lateralis and biceps femoral muscles. Using a micro-driver (Stryker, Kalamazoo, Mich.), four canals were drilled on each femur with 2 mm interface. SNPSA K-wires were implanted into each predrilled canal. The overlying muscle and fascia were closed with 4-0 Vicryl absorbable suture to secure the implant in place. Following surgery, the animals were housed in separate cages and allowed to eat and drink adlibitum. Weight bearing was started immediately postoperatively, and the animals were monitored daily. Buprenorphine was administered for 2 days as an analgesic, but no antibiotic was administered. Three rats were used in every treatment group. No obvious signs of bone formation were shown in rat FCs implanted with 0%-SNPSA up to 8 weeks post-surgery (A). In contrast, radiography revealed significant bone formation (blue arrows) around 2%-SNPSAs implanted in rat FCs (B).

FIGS. 16A and 16B exemplary radiographic images of contaminated 0%- and 2%-SNPSA implants in rat FCs, based on experiments with 103 CFU S. aureus Mu50 (a) or P. aeruginosa PAO-1 (b). All surgical procedures were approved by the UCLA Office of Animal Research Oversight (protocol #2008-073). Using aseptic technique, a 25-30 mm longitudinal incision was made over the anterolateral aspect of the left femur of 12-week old SD rats. The femoral shaft was then exposed by separating the vastus lateralis and biceps femoral muscles. Using a micro-driver (Stryker, Kalamazoo, Mich.), four canals were drilled on each femur with 2 mm interface. SNPSA K-wires were implanted into each predrilled canal. For bacterial inoculation, $10^3$ CFU *S. aureus* Mu50 (B) or *P. aeruginosa* PAO-1 (B) in 10 µl PBS ($10^5$ CFU/ml) was pipetted into the canal before implantation. After inoculation, the overlying muscle and fascia were closed with 4-0 Vicryl absorbable suture to secure the implant in place. Following surgery, the animals were housed in separate cages and allowed to eat and drink adlibitum. Weight bearing was started immediately postoperatively, and the animals were monitored daily. Buprenorphine was administered for 2 days as an analgesic, but no antibiotic was administered. Three rats were used in every treatment group. $10^3$ CFU *S. aureus* Mu50 (B) or *P. aeruginosa* PAO-1 (B) in 10 µl PBS ($10^5$ CFU/ml) was pipetted into the canal before implantation for bacterial invasion. Radiographic evidence of osseous destruction (red arrows), without any obvious signs of bone formation up to 8 weeks post-surgery, was detected in the contaminated 0%-SNPSA group. In contrast, significant bone formation surrounding 2%-SNPSAs implanted in rat FCs at week 8 post-implantation (shown as blue arrows in 2D resolution microCT images), without significant osteolysis, was detected. Newly formed bone around 2%-SNPSA implants was highlighted in 3D microCT reconstruction images (blue shading).

FIGS. 17A through 17E illustrate exemplary histological and immunohistochemical (IHC) analysis of contaminated 0%- and 2%-SNPSA implants in rat FCs at 8 weeks after implantation. $10^3$ CFU *S. aureus* Mu50 or *P. aeruginosa* PAO-1 in 10 µl PBS ($10^5$ CFU/ml) was pipetted into the canal before implantation for bacterial invasion. Taylor-modified Brown and Brenn Gram staining (A) and Giemsa staining (B) revealed bacterial persistence (yellow dotted circles) with massive inflammatory cell infiltration (red arrowheads) in the intramedullary tissue around 0%-SNPSA implants in rat FCs. In contrast, no bacterial survival was evident around 2%-SNPSA implants in the same situation, and inflammatory cell infiltration in the intramedullary tissues around the implants was minimal. Consistent with the radiographic analysis, only minimal bone formation around the 0%-SNPSA groups was observed, whereas significant bone formation (blue arrows) was detected around 2%-SNPSA implants, as shown by H&E staining (D), Masson's Trichrome staining (D), and immunostaining of high-intensity OCN signals (E). Yellow scale bar=50 µm (shown in 17A); red scale bar=100 µm (shown in 17B); white scale bar=500 µm (shown in 17C); black scale bar=200 µm (shown in 17D and 17E).

DETAILED DESCRIPTION OF THE INVENTION

Definitions

Unless otherwise noted, terms are to be understood according to conventional usage by those of ordinary skill in the relevant art.

As used herein, the term "device" encompasses any device that can be placed within a mammal (e.g., a human, a cow, a dog, etc.) via a surgical or otherwise invasive procedure. In some embodiments, the term device is used interchangeably with the term "scaffold", "fixture" or "implant."

As used herein, the term "nanoparticle" encompasses small particles having sizes that are often smaller than micrometers. Exemplary nanoparticle configurations include but are not limited to nanoclusters (e.g., having at least one dimension between 1 and 100 nanometers and a narrow size distribution); nanopowders (e.g., agglomerates of ultrafine particles, nanoparticles, or nanoclusters); nanocrystals (nanometer-sized single crystals, or single-domain ultrafine particles, or groups of crystals). In some embodiments, the size of a nanoparticle will be determined by its smallest dimension. It will be understood that the term nanoparticle does not imply that a spherical configuration. For example, silver nanoparticles do not necessarily suggest a spherical or ball-like shape. Indeed, silver nanoparticles can be spherical, fiber-like, branch-like, cluster-like, or of an irregular shape. In this application, the term "nanosilver" is used interchangeably as "silver nanoparticles."

As used herein, the term "biocompatible" refers to a property of a material characterized by it, or its physiological degradation products, being not, or at least minimally, toxic to living tissue; not, or at least minimally and reparably, otherwise injurious living tissue; and/or not, or at least minimally and controllably, causative of an immunological reaction in living tissue. With regard to salts, both the cation and anion must be biocompatible.

As used herein, the term "biodegradation" includes all means by which a polymer can be disposed of in a patient's body, which includes bioabsorption, resorption, etc. Degradation occurs through hydrolysis, chemical reactions, or enzymatic reactions. Biodegradation can take place over an extended period of time, for example over 2-3 years. The term "biostable" means that the polymer does not biodegrade or bioabsorb under physiological conditions, or biodegrade or bioabsorb very slowly over a very long period of time, for example, over 5 years or over 10 years.

As used herein, the term "coating" is broadly defined as a layer of substance or material that is deposited over a surface of a device (e.g., a scaffold or an implant). In some embodiments, a polymeric matrix comprising silver nanoparticles is deposited as a coating upon a metal or polymeric device. In some embodiments, the coating comprises one or more layers in any combination, with one or more of such layers comprising silver nanoparticles. In some embodiments, multiple layers including but not limited to a primer layer, which may improve adhesion of subsequent layers on the implantable substrate or on a previously formed layer; (b) a reservoir layer, which may comprise a polymer and nanoparticles in the presence or absence a therapeutic agent or, alternatively, a polymer free agent; (c) a topcoat layer, which may serve as a way of controlling the accessibility of the silver nanoparticles or the rate of release of the therapeutic agent; and (d) a biocompatible finishing layer, which may improve the biocompatibility of the coating. In some embodiments, the polymer matrix and polymer substrate can be completely absorbed by the body, preferably at different rate.

Unless otherwise noted, terms are to be understood according to conventional usage by those of ordinary skill in the relevant art.

Making of the Devices

Provided herein are compositions and methods for making devices (e.g., scaffolds and implants) that have antimicrobial properties and other additional properties that are advantageous for cell/tissue development and wound healing. Examples of the additional properties include but are not limited to osteoinductive and/or osteoconductive properties.

In some embodiments, an antimicrobial agent is deposited on a device (e.g., a scaffold, a fixture, or an implant) over at least a portion of the device. It will be understood that the antimicrobial agent will be chosen to suit the specific purpose.

In some embodiments, a composition comprising an antimicrobial agent is deposited on a pre-made device (e.g., a scaffold, a fixture, or an implant) to form a coating over at least a portion of the device.

In some embodiments, when associated with an implantable device, the antimicrobial agent is also chosen for its ability in selectively promoting growth of certain cells of a recipient of an implantable device while inhibiting the growth of harmful organisms as well as cells whose growth is undesirable.

In some embodiments, the antimicrobial agent comprises silver nanoparticles. Silver has sustained and long-lasting antimicrobial properties. Silver nanoparticles can be formed in a variety of ways and in different configurations. In some embodiments, nanoparticles of silver itself can be formed before being attached to an implantable device. In some embodiments, nanoparticles comprising silver and other material (e.g., a polymeric material); for example, nanoparticles can be formed using the polymeric material with silver embedded therein. Antiseptics such as silver have long been used in various fields of medicine. For example, continuous application of electrically active silver dressings is an effective adjunct in the treatment of chronic bone infection when combined with adequate surgical debridement, thereby reducing the need for prolonged systemic antibiotics. Silver targets a broad spectrum of Gram-positive and Gram-negative bacteria by attaching to specific thiol groups found in a variety of structural and functional bacterial proteins. In addition, silver resistance requires at least three separate mutations in three different bacterial systems—all within one generation of bacteria; thus, silver-resistant bacteria are rarely observed in hospital microbial germ flora.

In some embodiments, pure silver particles can be produced in a nanoscale form. Due to their greater surface-to-mass ratio, silver nanoparticles exhibit greater solubility, chemical reactivity, and antibacterial activity compared to conventional silver preparations. Previously, we have demonstrated in vitro that silver nanoparticles are non-toxic and effective as antimicrobials, and that silver nanoparticle-based bone grafts combined with BMP-2 successfully regenerate bone in vivo in a rat femoral segmental defect (FSD) infected with *S. aureus* Mu50, an MRSA strain with intermediate vancomycin resistance.

In some embodiments, the polymeric material is biocompatible. In some embodiments, the polymeric material is bioabsorbable. In some embodiments, the polymeric material is biodegradable.

In some embodiments, one or more additional coatings can be deposited over the silver-containing nanoparticles or a coating comprising the silver-containing nanoparticles. The additional coating can be formed by one or more polymeric material that is biocompatible, bioabsorbable and/or biodegradable.

Nanoparticles (e.g., of silver or with silver embedded therein) of a wired range of sizes can be used to impart antimicrobial property to a medical device (e.g., an implantable device). In some embodiments, the nanoparticles have a mean size of about 1000 nm or smaller, about 900 nm or smaller, about 800 nm or smaller, about 700 nm or smaller, about 600 nm or smaller, about 500 nm or smaller, about 400 nm or smaller, about 300 nm or smaller, about 250 nm or smaller, about 200 nm or smaller, about 180 nm or smaller, about 150 nm or smaller, about 120 nm or smaller, about 100 nm or smaller, about 90 nm or smaller, about 80 nm or smaller, about 70 nm or smaller, about 60 nm or smaller, about 50 nm or smaller, about 45 nm or smaller, about 40 nm or smaller, about 35 nm or smaller, about 32 nm or smaller, about 30 nm or smaller, about 28 nm or smaller, about 25 nm or smaller, about 22 nm or smaller, about 20 nm or smaller, about 18 nm or smaller, about 15 nm or smaller, about 12 nm or smaller, about 10 nm or smaller, about 8 nm or smaller, about 5 nm or smaller, or about 2 nm or smaller. In some embodiments, the nanoparticles used have a size between 20 nm to 40 nm.

In some embodiments, about 10% or more of the nanoparticles have sizes that are comparable to the mean size of the population of nanoparticles. In some embodiments, about 20% or more of the nanoparticles have sizes that are comparable to the mean size of the population of nanoparticles. In some embodiments, about 30% or more of the nanoparticles have sizes that are comparable to the mean size of the population of nanoparticles. In some embodiments, about 35% or more of the nanoparticles have sizes that are comparable to the mean size of the population of nanoparticles. In some embodiments, about 40% or more of the nanoparticles have sizes that are comparable to the mean size of the population of nanoparticles. In some embodiments, about 45% or more of the nanoparticles have sizes that are comparable to the mean size of the population of nanoparticles. In some embodiments, about 50% or more of the nanoparticles have sizes that are comparable to the mean size of the population of nanoparticles. In some embodiments, about 55% or more of the nanoparticles have sizes that are comparable to the mean size of the population of nanoparticles. In some embodiments, about 60% or more of the nanoparticles have sizes that are comparable to the mean size of the population of nanoparticles. In some embodiments, about 65% or more of the nanoparticles have sizes that are comparable to the mean size of the population of nanoparticles. In some embodiments, about 70% or more of the nanoparticles have sizes that are comparable to the mean size of the population of nanoparticles. In some embodiments, about 75% or more of the nanoparticles have sizes that are comparable to the mean size of the population of nanoparticles. In some embodiments, about 80% or more of the nanoparticles have sizes that are comparable to the mean size of the population of nanoparticles. In some embodiments, about 85% or more of the nanoparticles have sizes that are comparable to the mean size of the population of nanoparticles. In some embodiments, about 80% or more of the nanoparticles have sizes that are comparable to the mean size of the population of nanoparticles. In some embodiments, about 95% or more of the nanoparticles have sizes that are comparable to the mean size of the population of nanoparticles. In some embodiments, about 98% or more of the nanoparticles have sizes that are comparable to the mean size of the population of nanoparticles. In some embodiments, about 99% or more of the nanoparticles have sizes that are comparable to the mean size of the population of nanoparticles.

In some embodiments, a device (e.g., with an antimicrobial coated on its surface or embedded within) provided herein is an osteoconductive scaffold that promotes osteoblastic cell ingrowth and at the same time prevents fibroblastic cell ingrowth. Advantageously, silver nanoparticles are preferentially toxic to fibroblasts rather than osteoblasts.

Exemplary polymeric material that can be used here include but are not limited to a biocompatible or bioabsorbable polymer that is one or more of poly(DL-lactide), poly(L-lactide), poly(L-lactide), poly(L-lactide-co-D,L-lactide), polymandelide, polyglycolide, poly(lactide-co-glycolide), poly(D,L-lactide-co-glycolide), poly(L-lactide-co-glycolide), poly(ester amide), poly(ortho esters), poly(glycolic acid-co-trimethylene carbonate), poly(D,L-lactideco-trimethylene carbonate), poly(trimethylene carbonate), poly(lactide-co-caprolactone), poly(glycolide-co-caprolactone), poly(tyrosine ester), polyanhydride, derivatives thereof. In some embodiments, the polymeric material comprises a combination of these polymers.

In some embodiments, the polymeric material comprises poly(D,L-lactide-co-glycolide). In some embodiments, the polymeric material comprises poly(D,L-lactide). In some embodiments, the polymeric material comprises poly(L-lactide).

Additional exemplary polymers include but are not limited to poly(D-lactide) (PDLA), polymandelide (PM), polyglycolide (PGA), poly(L-lactide-co-D,L-lactide) (PLDLA), poly(D,L-lactide) (PDLLA), poly(D,L-lactide-co-glycolide) (PLGA) and poly(L-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

In some embodiments, polymers that are more flexible or that have a lower modulus that those mentioned above may also be used. Exemplary lower modulus bioabsorbable polymers include, polycaprolactone (PCL), poly(trimethylene carbonate) (PTMC), polydioxanone (PDO), poly(3-hydrobutyrate) (PHB), poly(4-hydroxybutyrate) (P4HB), poly(hydroxyalkanoate) (PHA), and poly(butylene succinate), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) or poly(L-lactide)-co-polycaprolactone (PLLA-co-PCL). The composition of a blend can include 1-5 wt % of low modulus polymer.

More exemplary polymers include but are not limited to at least partially alkylated polyethyleneimine (PEI); at least partially alkylated poly(lysine); at least partially alkylated polyornithine; at least partially alkylated poly(amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins, and mixtures thereof.

Additional examples of biocompatible biodegradable polymers include, without limitation, polycaprolactone, poly(L-lactide), poly(D,L-lactide), poly(D,L-lactide-co-PEG) block copolymers, poly(D,L-lactide-co-trimethylene carbonate), poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), poly-carbonates, polyurethanes, polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate), MED610, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

In some embodiments, polyethylene is used to construct at least a portion of the device. For example, polyethylene can be used in an orthopedic implant on a surface that is designed to contact another implant, as such in a joint or hip replacement. Polyethylene is very durable when it comes into contact with other materials. When a metal implant moves on a polyethylene surface, as it does in most joint replacements, the contact is very smooth and the amount of wear is minimal. Patients who are younger or more active may benefit from polyethylene with even more resistance to wear. This can be accomplished through a process called crosslinking, which creates stronger bonds between the elements that make up the polyethylene. The appropriate amount of crosslinking depends on the type of implant. For example, the surface of a hip implant may require a different degree of crosslinking than the surface of a knee implant.

Additional examples of polymeric materials can be found, for example, in U.S. Pat. No. 6,127,448 to Domb, entitled "Biocompatible Polymeric Coating Material;" US Pat. Pub. No. 2004/0148016 by Klein and Brazil, entitled "Biocompatible Medical Device Coatings;" US Pat. Pub. No. 2009/0169714 by Burghard et al., entitled "Biocompatible Coatings for Medical Devices;" U.S. Pat. No. 6,406,792 to Briquet et al., entitled "Biocompatible Coatings;" US Pat. Pub. No. 2008/0003256 by Martens et al., entitled "Biocompatible Coating of Medical Devices;" each of which is hereby incorporated by reference herein in its entirety.

In some embodiments, a portion of or the entire device is formed by one or more the aforementioned polymeric materials provided herein. In some embodiments, the polymeric material used to form the device further comprises an antimicrobial agent such that the antimicrobial agent is embedded as a part of the device itself. In some embodiments, a biomedical material such as titanium, silicone or apatite is used to modify the surface of the device such that the device is biocompatible and does not trigger adverse reactions in a patient (e.g., a recipient of an implant).

In some embodiments, a portion of or the entire device is made from a metal material. Exemplary metal materials include but are not limited to stainless steel, chromium, a cobalt-chromium alloy, Tantalum, titanium, a titanium alloy and combinations thereof.

Stainless steel is a very strong alloy, and is most often used in implants that are intended to help repair fractures, such as bone plates, bone screws, pins, and rods. Stainless steel is made mostly of iron, with other metals such as chromium or molybdenum added to make it more resistant to corrosion. There are many different types of stainless steel. The stainless steels used in orthopedic implants are designed to resist the normal chemicals found in the human body. Cobalt-chromium alloys are also strong, hard, biocompatible, and corrosion resistant. These alloys are used in a variety of joint replacement implants, as well as some fracture repair implants, that require a long service life. While cobalt-chromium alloys contain mostly cobalt and chromium, they also include other metals, such as molybdenum, to increase their strength. Titanium alloys are considered to be biocompatible. They are the most flexible of all orthopedic alloys. They are also lighter weight than most other orthopedic alloys. Consisting mostly of titanium, they also contain varying degrees of other metals, such as aluminum and vanadium. Pure titanium may also be used in some implants where high strength is not required. It is used, for example, to make fiber metal, which is a layer of metal fibers bonded to the surface of an implant to allow the bone to grow into the implant, or cement to flow into the implant, for a better grip. Tantalum is a pure metal with excellent physical and biological characteristics. It is flexible, corrosion resistant, and biocompatible.

It will be understood by one of skill in the art that the method and composition provided herein can be used to impart antimicrobial and/or any other advantageous property to any device that is used as a surgical implant. In some embodiments, devices provided herein include medical implants, scaffolds and/or surgical instruments. Exemplary medical implants include but are not limited to stents, balloons, valves, pins, rods, screws, discs, and plates. Exemplary medical implants include but are not limited to an artificial replacement of a body part such as a hip, a joint, etc.

In some embodiments, the devices include an implantable intervertebral device (e.g., a cervical fusion device).

In some embodiments, devices disclosed herein include those associated with dental surgeries, including but not limited to a disc, a bridge, a retainer clip, a screw, a housing, a bone graft, and/or a crown.

In some embodiments, devices disclosed herein include those associated with orthopedic surgeries, including, for example, intramedullary rods, temporary and permanent pins and implants, bone plates, bone screws and pins, and combinations thereof.

In some embodiments, a device provided herein further comprises a bioactive agent such as a graft, an osteoconductive or osteoinductive graft material, a bone morphogenetic protein, a growth factor and a buffer material. Exemplary osteoconductive or osteoinductive graft materials include but are not limited to hydroxyapatite BMP, growth factors (e.g., transforming growth factor (TGF) beta-1, 2 and 3, BMP-2, BMP-3, BMP-7, insulin-like growth factor (IGF)-1, and possibly vascular endothelial growth factor (VEGF)), hydroxyapatite or calcium phosphate.

Additional information on implantable medical devices and osteoinductive materials can be found, for example, in United States Patent Publication No. 2009/0012620 by Youssef J., et al. and entitled "Implantable Cervical Fusion Device;" U.S. Pat. No. 5,348,026 to Davidson and entitled "Osteoinductive Bone Screw;" Barradas A. et al., 2011, "Osteoinductive Biomaterials: Current Knowledge of Properties, Experimental Models and Biological Mechanisms," European Cells and Materials 21:407-429; U.S. Pat. No. 7,485,617 to Pohl J. et al. and entitled "Osteoinductive Materials," United States Patent Publication No. 2011/0022180 by Melkent A., et al. and entitled "Implantable Medical Devices;" United States Patent Publication No. 2005/0010304 by Jamali, A. and entitled "Device and Method for Reconstruction of Osseous Skeletal Defects;" United States Patent Publication No. 2010/0036502 by Svrluga R. et al. and entitled "Medical Device for Bone Implant and Method for Producing Such Device;" U.S. Pat. No. 5,672,177 to E. Seldin and entitled "Implantable Bone Distraction Device;" and U.S. Pat. No. 4,611,597 to W. Kraus and entitled "Implantable Device for the Stimulation of Bone Growth;" each of which is hereby incorporated by reference in its entirety.

In some embodiments, the polymeric material forms a coating on the device before an antimicrobial agent is subsequently deposited.

In some embodiments, the antimicrobial agent is dispersed in the polymeric material before the mixture is deposited on the device to form a coating.

In some embodiments, the antimicrobial agent is dispersed in the polymeric material before the mixture is used to form a portion of the device or the entire device itself.

In some embodiments, the antimicrobial agent constitutes about 0.1% or less by weight, about 0.2% or less by weight, about 0.3% or less by weight, about 0.4% or less by weight, about 0.5% or less by weight, about 0.6% or less by weight, about 0.7% or less by weight, about 0.8% or less by weight, about 0.9% or less by weight, about 1.0% or less by weight, about 1.1% or less by weight, about 1.2% or less by weight, about 1.3% or less by weight, about 1.4% or less by weight, about 1.5% or less by weight, about 1.6% or less by weight, about 1.7% or less by weight, about 1.8% or less by weight, about 1.9% or less by weight, about 2.0% or less by weight, about 2.1% or less by weight, about 2.2% or less by weight, about 2.3% or less by weight, about 2.4% or less by weight, about 2.5% or less by weight, about 2.6% or less by weight, about 2.7% or less by weight, about 2.8% or less by weight, about 2.9% or less by weight, about 3.0% or less by weight, about 3.2% or less by weight, about 3.5% or less by weight, about 3.8% or less by weight, about 4.0% or less by weight, about 4.5% or less by weight, about 5.0% or less by weight, about 7.0% or less by weight, about 10.0% or less by weight, about 15.0% or less by weight, about 20.0% or less by weight, about 30.0% or less by weight, about 40.0% or less by weight, about 50.0% or less by weight of the total weight of the mixture.

In some embodiments, the antimicrobial agent constitutes about 0.1% or less by weight, about 0.2% or less by weight, about 0.3% or less by weight, about 0.4% or less by weight, about 0.5% or less by weight, about 0.6% or less by weight, about 0.7% or less by weight, about 0.8% or less by weight, about 0.9% or less by weight, about 1.0% or less by weight, about 1.1% or less by weight, about 1.2% or less by weight, about 1.3% or less by weight, about 1.4% or less by weight, about 1.5% or less by weight, about 1.6% or less by weight, about 1.7% or less by weight, about 1.8% or less by weight, about 1.9% or less by weight, about 2.0% or less by weight, about 2.1% or less by weight, about 2.2% or less by weight, about 2.3% or less by weight, about 2.4% or less by weight, about 2.5% or less by weight, about 2.6% or less by weight, about 2.7% or less by weight, about 2.8% or less by weight, about 2.9% or less by weight, about 3.0% or less by weight, about 3.2% or less by weight, about 3.5% or less by weight, about 3.8% or less by weight, about 4.0% or less by weight, about 4.5% or less by weight, about 5.0% or less by weight, about 7.0% or less by weight, about 10.0% or less by weight, about 15.0% or less by weight, about 20.0% or less by weight, about 30.0% or less by weight, about 40.0% or less by weight, about 50.0% or less by weight of the total weight of the polymeric material.

It will be understood by one skill in the art that the device can be coated in any manner known in the art. In some embodiments, the portion of the device upon which an antimicrobial agent (e.g., alone or in combination with a polymeric material) is deposited constitutes less than about 2%, less than about 5%, less than about 8%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, less than about 98%, less than about 99% of a surface of the device, where the surface is in contact with a biological/cellular environment (for example, at a site where the device is implanted). In some embodiments, the entire contact surface is substantially covered with the composition.

In some embodiments, the device has more than one contact surfaces. It will be understood that the antimicrobial agent can be deposited on a portion of any one or all of these contact surfaces at any percentage as disclosed herein.

In some embodiments, an antimicrobial agent (e.g., alone or in combination with a polymeric material) is deposited upon a contact surface of the device, continuously or discontinuously. For example, an antimicrobial agent (e.g., alone or in combination with a polymeric material) can be deposited continuously over less than about 2%, less than about 5%, less than about 8%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, less than about 98%, less than about 99% of a contact surface of the device.

In some embodiments, an antimicrobial agent (e.g., alone or in combination with a polymeric material) can be deposited discontinuously over a contact surface of the device; for example the antimicrobial agent can be deposited over the contact surface as discrete dots, circles, squares, triangles, ovals, or in any other suitable forms or pattern, rendering a total surface area being covered of less than about 2%, less than about 5%, less than about 8%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, less than about 98%, less than about 99% of a contact surface of the device.

In some embodiments, one or more therapeutic agents are embedded or impregnated in a device provided herein. In some embodiments, one or more therapeutic agents are embedded or impregnated the polymeric material that forms the device itself or a coating on the surface of a device. In some embodiments, one or more therapeutic agents are added as an additional coating over silver nanoparticles or a coating comprising the silver nanoparticles. In some embodiments, the therapeutic agent can be mixed or dispersed in part of or throughout the polymer scaffold or implant.

It will be understood that any therapeutic agent can be used in combination with the silver nanoparticles provided herein. Exemplary therapeutic agents include but are not limited to one or more anti-microbial agents: aminoglycosides (such as amikacin, gentamicin, kanamycin, neomycin, netilmicin, tobramycin, and/or paromomycin); ansamycins (such as geldanamycin and/or herbimycin); carbacephem (such as loracarbef), carbapenems (such as ertapenem, doripenem, imipenem/cilastatin, and/or meropenem); cephalosporins (such as cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil and/or ceftobiprole); glycopeptides (such as teicoplanin, vancomycin and/or telavancin); lincosamides (such as clindamycin and/or lincomycin); lipopeptide such as daptomycin; macrolides (such as azithromycin, clarithromycin, dirithromycin, erythromycin, roxithromycin, troleandomycin, telithromycin, spectinomycin, spiramycin); monobactams (such as aztreonam, nitrofurans, furazolidone and/or nitrofurantoin), penicillins or penicillin combinations (such as amoxicillin, ampicillin, azlocillin, carbenicillin, cloxacillin, dicloxacillin, flucloxacillin, mezlocillin, methicillin, nafcillin, oxacillin, penicillin v, piperacillin, penicillin g, temocillin, ticarcillin, amoxicillin/clavulanate, ampicillin/sulbactam, piperacillin/tazobactam and/or ticarcillin/clavulanate); polypeptides (such as bacitracin, colistin, and/or polymyxin b); quinolones (such as ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin and/or temafloxacin); sulfonamides (such as mafenide, sulfonamidochrysoidine, sulfacetamide, sulfadiazine, silver sulfadiazine, sulfamethizole, sulfamethoxazole, sulfanilimide, sulfasalazine, sulfisoxazole and/or trimethoprim-sulfamethoxazole-co-trimoxazole); tetracyclines (such as demeclocycline, doxycycline, minocycline, oxytetracycline and/or tetracycline); drugs against mycobacteria such as clofazimine, dapsone, capreomycin, cycloserine, ethambutol, ethionamide, isoniazid, pyrazinamide, rifampicin, rifabutin, rifapentine, streptomycin); arsphenamine, chloramphenicol, fosfomycin, fusidic acid, linezolid, metronidazole, mupirocin, platensimycin, quinupristin/dalfopristin, rifaximin, thiamphenicol, tigecycline, timidazole, trimethoprim, or combinations thereof.

Exemplary therapeutic agents also include but are not limited to one or more anti-inflammatory agents or any other agents that can be beneficial for the healing of the surgical site or promoting desired growth and development.

In some embodiments, one or more bioactive agents are embedded or impregnated in a device provided herein. In some embodiments, one or more bioactive agents are embedded or impregnated the polymeric material that forms the device itself or a coating on the surface of a device.

In some embodiments, one or more bioactive agents are associated with a device provided herein. In some embodiments, one or more bioactive agents are contained in a compartment of the device.

Exemplary bioactive agents include but are not limited to cells, a biocompatible buffer, growth media or extracellular matrices, growth factors, cytokines, includes metabolites, any small molecules or macromolecules.

In some embodiments, embryonic stem cells (e.g., blastocyst-derived) are cultured and produced within an implantable device as disclosed herein. In some embodiments, blastocyst-derived stem cells isolated from the inner cell mass of blastocysts can be used. In some embodiments, adult stem cells or somatic stem cells, which are found in various tissues (e.g., from bone marrow derived sources), can also be used. Additional adult stem cells include but are not limited to hematopoietic stem cells, mammary stem cells, intestinal stem cells, mesenchymal stem cells, endothelial stem cells, neural stem cells, olfactory adult stem cells, neural crest stem cells, and testicular cells.

In some embodiments, non-stem cells are used. Potentially, all of the 200 or so mammalian cell types within the body can be used in an implantable device as disclosed herein. Exemplary cells include but are not limited to, for example, cells found within a non-embryonic adult, such as insulin secreting cells (e.g., from adults or cadavers) or hepatocytes; islets of Langerhands; cells via somatic cell nuclear transfer (SCNT cells); cells via induced pluripotent stem cells (iPSs cells) either derived by genetic or chemical means; and cells from umbilical cord blood (UCB) cells.

In some embodiments, donor cells are used, including autologous (self) cells or non-autologous cells (e.g., allogenic or xenogenic cells from unrelated donors or other species).

In some embodiments, the cells or tissue used in the device can be suspended in a liquid trapped within a sub-compartment, adhered to the inner walls of the compartment or immobilized on an appropriate support structure provided within the compartment. For example, the cells can be embedded in a gel matrix (e.g., agar, alginate, chitosan, polyglycolic acid, polylactic acid, and the like). In some embodiments, a porous scaffold (e.g., an alignate scaffold) can be used to seed the content within a compartment or sub-compartments of an implantable device. In some embodiments, microcapsules or microbeads can be used to encapsulate or capture cells in the cellular compartment.

In some embodiments, a commercially available growth medium or matrix for mammalian cells is used. For example, Matrigel™ is the trade name for a gelatinous protein mixture secreted by Engelbreth-Holm-Swarm (EHS) mouse sarcoma cells and marketed by BD Biosciences and by Trevigen Inc. under the name Cultrex BME. This mixture resembles the complex extracellular environment found in many tissues and is used by cell biologists as a substrate for cell culture. Components of a standard growth medium or matrix for mammalian cells include but are not limited to extracellular matrix components, growth factors, various cytokines, and one or more pharmaceutical agents, as listed in Table 1.

TABLE 1

| Compositions of exemplary biochemical composition. Extracellular Matrix components |
|---|
| Undefined media |
| Extract from the EHS tumor (e.g., Matrigel ™ from BD Biosciences) Growth Factor Reduced Matrigel ™ High Concentration Matrigel ™ Exemplary individual components: |
| Laminin Entactin 1 Collagens I-VI Heparin sulfate proteoglycans agar alginate chitosan polyglycolic acid polylactic acid |

Exemplary growth factors include but are not limited to adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF) 1, 2, 3, glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF)

and other neurotrophins, platelet-derived growth factor (PDGF), thrombopoietin (TPO), transforming growth factor alpha (TGF-α), transforming growth factor beta (TGF-β), tumor necrosis factor-alpha (TNF-α), vascular endothelial growth factor (VEGF), placental growth factor (PlGF), fetal bovine somatotrophin (FBS), IL-1, IL-2, IL-3, IL-4, IL-5, IL-6 and IL-7.

Exemplary cytokines include but are not limited to interleukin 2, interleukin 15 preprotein, tumor necrosis factor (ligand) superfamily, member 18, interleukin 26, interleukin 20, interleukin 22, interferon epsilon 1, interferon-gamma, colony stimulating factor 2, interleukin 19 isoform 2, tumor necrosis factor (ligand) superfamily, member 4, interleukin 24 isoform 1, interferon, beta 1, fibroblast, interleukin 5, interleukin 13, growth hormone 2 isoform 1, interferon, omega 1, interleukin 12A, tumor necrosis factor (ligand) superfamily, member 10, interleukin 6 (interferon, beta 2), interferon, alpha 1, growth hormone 1 isoform 1, leptin, interleukin 1, beta proprotein, tumor necrosis factor alpha, interferon kappa, interleukin 3, interleukin 10, tumor necrosis factor (ligand) superfamily, member 15, prolactin, interleukin 28A, interleukin 17B, ciliary neurotrophic factor, thymic stromal lymphopoietin isoform 1, interleukin 4 isoform 1, interleukin 17E isoform 1, chemokine (C-C motif) ligand 16, interleukin 9, interleukin 1, alpha proprotein, chemokine (C-C motif) ligand 15, chemokine (C motif) ligand 2, tumor necrosis factor ligand superfamily, member 14 isoform 1, chemokine (C motif) ligand 1, chemokine (C-C motif) ligand 25, CD40 ligand, chemokine (C-X-C motif) ligand 13 (B-cell chemoattractant), interleukin 29, tumor necrosis factor (ligand) superfamily, member 8, and interleukin 28B.

Exemplary metabolites include but are not limited to alcohols (e.g., ethanol), amino acids (e.g., glutamic acid, aspartic acid), nucleotides (e.g., 5' guanylic acid), antioxidants (e.g., isoasorbic acid), organic acids (e.g., acetic acid, lactic acid), polyols (e.g., glycerol), vitamins (e.g., B2), minerals, and electrolytes. In some embodiments, metabolites also include secondary metabolites.

Exemplary small chemical molecules include any chemical compounds, including inorganic and organic compounds, for example, formaldehyde, acetylsalicylic acid, methanol, ibuprofen, and statins. Exemplary macromolecules include but are not limited to monoclonal and polyclonal antibodies, nucleic acid, lipid, fatty acid, and insulin.

In some embodiments, devices provided herein can be placed within any animal, including but not limited to a mammal (e.g., a human, a cow, a dog, a cat, a goat, a sheep, a monkey, a horse, a dolphin, a lion, a tiger, a rat, a mouse, an elephant, and etc.) via a surgical or otherwise invasive procedure.

Characteristics and Applications of Devices

Properties of the devices provided herein can be characterized by many means, including but not limited to, for example, surface free energy, protein adsorption level (in vitro, ex vivo or in vivo), osteoinductivity (in vitro, ex vivo or in vivo), antimicrobial activities (in vitro, ex vivo or in vivo).

Exemplary data by such characterization methods can be found in the Example Section.

Devices provided herein are less likely to introduce microbial infection themselves. Further, they can be for a variety of applications to reduce or eliminate microbial infections. In some embodiments, the devices are used to reduce or eliminate microbial infections associated with a surgical procedure.

In some embodiments, the devices (e.g., a scaffold, a fixture, or an implant) can be used to mask other reagents that may possibly cause microbial infection. In some embodiments, a device can be used to introduce cells or tissues into a mammalian recipient; for example, a carrier of stem cell material. In some embodiments, the devices further include materials that will support or promote the growth and/or development of such cells or tissues.

A General Process

The following outlines a general process in accordance with the present invention.

Synthesis of the Nanosilver Particle-PLGA Coating:

Nanosilver particles between 20 nm and 40 nm silver particles (QSI-Nano® Silver) were obtained from QuantumSphere, Inc. (Santa Ana, Calif.). The nanosilver-PLGA coating is manufactured using a solvent casting technique known in the art. Briefly, the desired amount of nanosilver will be mixed with 17.5% (w/v) PLGA [85:15 poly(lactic-co-glycolic acid, inherent viscosity: 0.64 dl/g in chloroform; Durect Co., Pelham, Ala.]-chloroform solution. The concentration of silver refers to the weight ratio of nanosilver mixed with PLGA.

Figures 2A, 2B:
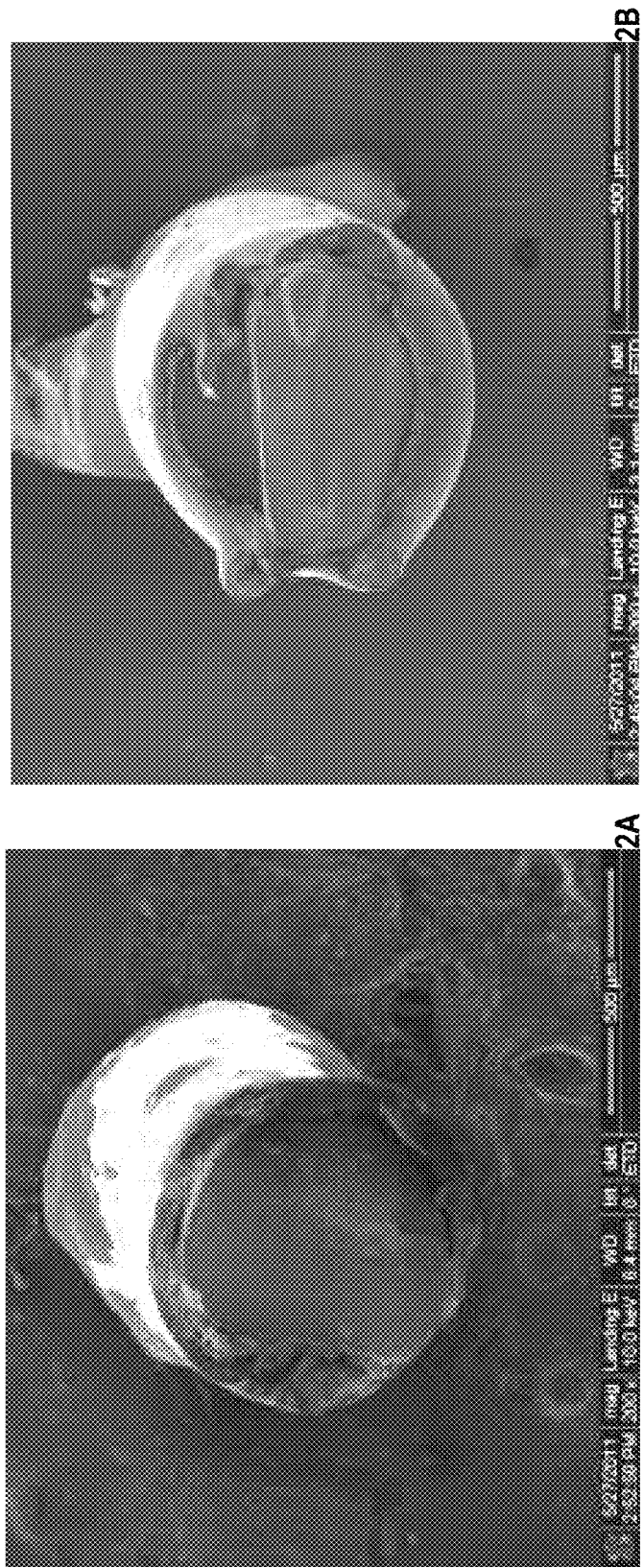
FIGS. 2A, 2B and 2C illustrate exemplary SEM images of nanosilver/PLGA coated K-wires before (A) and after bony insertion/removal (B). Note continued adherence of the nanosilver PLGA coating. (C) Light microscope and SEM images of SNPSA discs. A uniform layer of nanosilver/PLGA composite without aggregation was observed on the surface of stainless steel alloy. No significant difference was found between 0%- and 2%-SNPSA disc surfaces, while the surfaces of SNPSAs were much smoother than those of uncoated stainless steel alloy discs. Scale bar=50 µm FIGS. 3A through 3D exemplary surface free energy of SNPSAs. Dependency of the total surface free energy (A, $\gamma_s$), the dispersion component (B, $\gamma_s^d$), the non-dispersion component (C, $\gamma_s^{nd}$) and the polarity $$\left(D, \frac{\gamma_s^{nd}}{\gamma_s} \times 100\%\right)$$

Coating Nanosilver PLGA onto Titanium Implants:

The nanosilver/PLGA solution will be layered only onto titanium K-wire implants by immersion with a 5 minute interval between applications of each nanosilver PLGA layer. A 3-layer nanosilver/PLGA coating construct can be initially tested. The coated K-wires will be dried at 37° C. for at least 12 hours before use as we previously described6. We have successfully coated the nanosilver PLGA on K-wires (FIG. 2).

In Vitro Antimicrobial Activity:

In vitro antimicrobial activity of nanosilver particle-PLGA coatings will be determined using a standardized microplate proliferation assay as known in the art. Briefly, the nanosilver/PLGA coatings will be incubated with different logarithmic concentration of S. aureus in 200 μl of BHIB in 96-well plates at 37° C. for 1 h to allow adherence of the S. aureus to the coated K-wires. After incubation, coated K-wires will be rinsed with PBS to remove loosely attached bacteria, and then re-cultured in broth for 18 h at 37° C. in another 96-well microplate. During this second incubation step, the viable bacteria attached to the surface of the implants will start to multiply, releasing CFU into the wells. After removal of the implants, 100 μl of released bacteria will be transferred into another 96-well plate and then amplified by adding 100 μl of fresh broth for another 40 h at 37° C. Proliferation of the released cells will be measured at a wavelength of 595 nm using a microplate reader (Tecan, Durham, N.C.) to generate a time-proliferation curve. The coatings with the most potent antimicrobial activity will be evaluated in vivo.

In Vivo Efficacy of Nanosilver/-PLGA Coatings.

Different characterization techniques can be used to determine the most efficacious nanosilver/PLGA coating. For example, a mouse model of orthopedic implant infection with the endpoints i-iii: (i) In vivo bioluminescence imaging to measure bacterial burden; (ii) Biofilm formation and adherent bacteria; and (iii) Infection-induced inflammation. Nanosilver/PLGA coatings will be evaluated against an intermediate S. aureus inoculum (e.g. $1\times10^3$ CFU) that consistently produces an infection and biofilm formation on the implant and is detectable for 6 post-operative weeks. The nanosilver/-PLGA coatings can be compared to each other, the vehicle coating alone and to the current standard of care i.v. vancomycin prophylaxis used for MRSA by evaluating the following 4 groups: (1) Nanosilver/PLGA coating 1.0%;

(2) Nanosilver/PLGA 2.0%; (3) PLGA vehicle coating alone (no Nanosilver); and (4) PLGA vehicle coating alone+i.v. vancomycin (100 mg/kg) at 2 h pre- and 6 h post-operatively. Overall, these data show that nanosilver selectively inhibits fibroblast proliferation over osteoblast proliferation (e.g., FIGS. 13A and 13B).

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Figure 1:
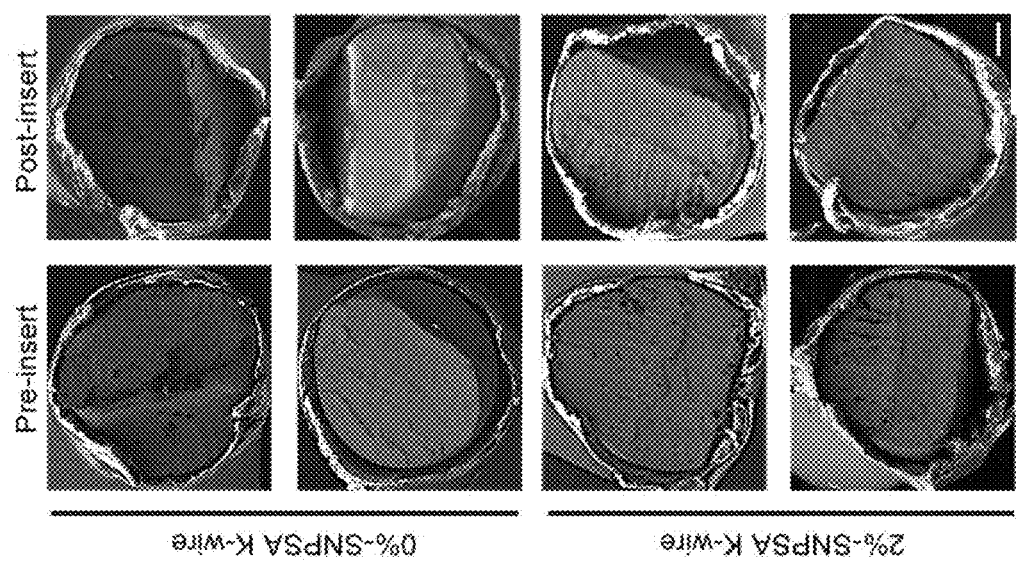
FIGS. 1A and 1B illustrate exemplary scan electron microscopy (SEM) images of nanosilver/poly(lactide-co-glycolide) (PLGA coated stainless steel alloy (SNPSA) Kirschner (K)-wires. A uniform layer nanosilver/PLGA composite was observed on the surface of stainless steel alloy. Aggregates of nanosilver were not found in nanosilver/PLGA composite layers containing up to 2% nanosilver (A). Light microscope images of SNPSA K-wires appear in the top panel. The thickness nanosilver/PLGA composite layer was 43.36±0.08 µm (B). Blue box shows the area magnified in the bottom panel. Placing SNPSA K-wires into the pre-reamed intramedullary canal did not considerably damage the coating. White scale bar=100 µm; black scale bar=25 µm.
Figure 1:
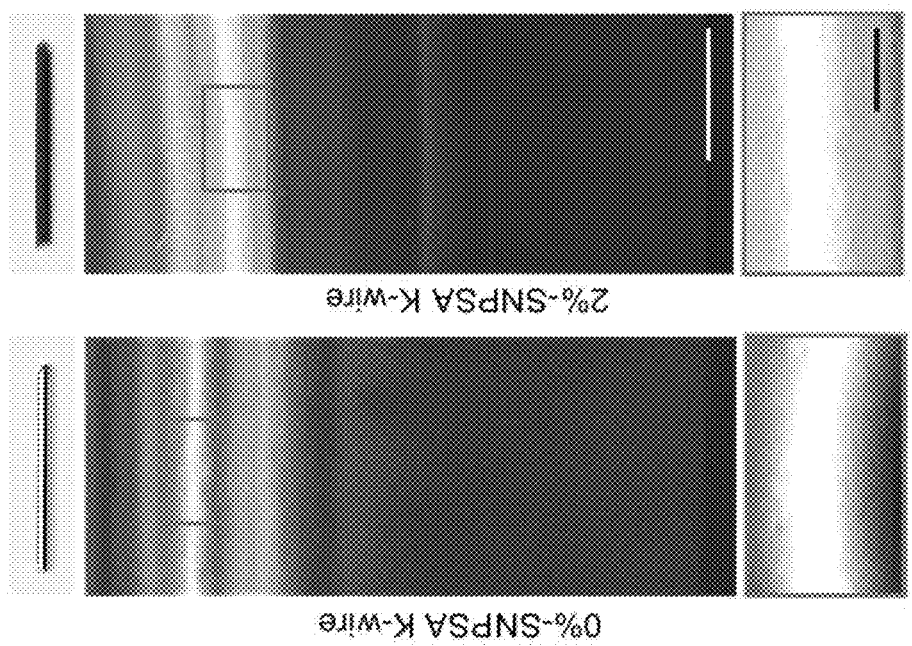

Stainless Steel Alloy Coating 20-40 nm-diameter spherical silver nanoparticles (QSI-Nano® Silver, QuantumSphere, Inc., Santa Ana, Calif.) were thoroughly mixed with 17.5% (w/v) PLGA (lactic: glycolic=85:15, inherent viscosity: 0.64 dl/g in chloroform; Durect Co., Pelham, Ala.) solution. The proportion of silver nanoparticles refers to the weight ratio of silver nanoparticles to PLGA. 316L stainless steel alloy Kirschner (K)-wire (length: 1 cm, diameter: 0.6 mm; Synthes. Monument, Colo.) and discs (thickness: 1.59 mm, diameter: 6.35 mm; Applied Porous Technologies, Inc., Tariffville, Conn.) were soaked in the silver nanoparticle/PLGA-chloroform solution for 30 s and air-dried completely. The soak-dry process was repeated three times for each SNPSA implant. After incubating for 12 h at 37° C. to ensure a uniform coating, SNPSAs were stored at −20° C. until use. Morphology of the SNPSA was evaluated by scanning electron microscopy (SEM; NovaNano SEM 230-D9064, FEI Company, Hillsboro, Oreg.) (FIGS. 1 and 2).

Example 2

Surface Free Energy

Surface free energy of SNPSAs was obtained from contact angle measurements. Contact angles of multiple standard liquids on the tested SNPSAs were measured using a contact angle analyzer (FTA125; First Ten Ångestroms, Portsmouth, Va.). In order to obtain an accurate description of the wetting behavior of various SNPSAs, the surface free energy of the solid ($\gamma_s$), was considered to be the sum of separate dispersion (γd) and non-dispersion ($\gamma_s^{nd}$) contributions. From this two-component model, the following relationship was derived from the dispersion $\gamma^d$ and non-dispersion (also known as 'polar') $\gamma^{nd}$ interactions between liquids and solids.

$$\gamma_L \times (\cos\theta + 1) = 2 \times (\gamma_L^d \times \gamma_s^d)^{\frac{1}{2}} + (\gamma_L^{nd} \times \gamma_s^{nd})^{\frac{1}{2}} \quad (1)$$

Eq. (1), known as the geometric mean model, allows the calculation of the solid surface free energy using the contact angle (θ) and the surface tension components of the standard liquids, where $\gamma_L$, $\gamma_L^d$, and $\gamma_L^d$ represent the surface tension and its dispersion and non-dispersion components of the standard liquids, respectively. The surface tension components of the standard liquids are listed in Table 2.

TABLE 2

Surface tension components of the standard liquids used.

| Standard liquids | Surface tension components (mN/m) | | |
|---|---|---|---|
| | $\gamma_L$ | $\gamma_L^d$ | $\gamma_L^{nd}$ |
| Water | 72.8 | 21.8 | 51.0 |
| Glycerol | 64.0 | 34.0 | 30.0 |
| Formamide | 58.0 | 39.0 | 19.0 |
| Ethylene glycol | 48.0 | 29.0 | 19.0 |

Example 3

In Vitro Antimicrobial Activity

The Gram-positive vancomycin-intermediate *S. aureus* (VISA/MRSA) strain Mu50 (ATCC 700699) was cultured in brain heart infusion broth (BHIB; BD, Sparks, Md.) at 37° C.; while biofilm-forming, Gram-negative opportunistic pathogen *P. aeruginosa* PAO-1 (ATCC 15692) was cultured in Luria Bertani broth (LB; Fisher Scientific, Hampton, N.H.) at 30° C. $10^3$, $10^4$, and $10^5$ colony forming units (CFU) of bacteria were suspended in 1 ml culture broth and incubated with the SNPSA K-wires at 225 rpm on a shaker for 1, 2, 6, and 24 hours.

At the end of the incubation, Mu50 and PAO-1 bacteria attached to the surface were collected by 0.9% saline solution and plated onto 10-cm BHIB or LB culture medium plates overnight, respectively.

After 18 h incubation, the number of colonies on each plate was counted and the total viable CFU load was determined.

Example 4

Ex Vivo Antimicrobial Activity

Femurs isolated from 12-week old male 129/sv mice were used to assay SNPSA antimicrobial activity ex vivo. Briefly, after locating the femoral intercondylar notch, an intramedullary canal was manually reamed into the distal femur with a 25-gauge needle. A SNPSA K-wire was then placed into the intramedullary canal with 2 μl Mu50 or PAO-1 bacteria suspended in phosphate buffered saline (PBS, pH 7.2; Invitrogen, Carlsbad, Calif.).

Femurs with implants were then placed on 100-μm cell strainers (BD) inside 6-well culture plates containing 2 ml α-minimal essential medium (α-MEM; Invitrogen) supplemented with 1% HT supplement (Invitrogen) and fetal bovine serum (FBS; Invitrogen).

Figure 12:
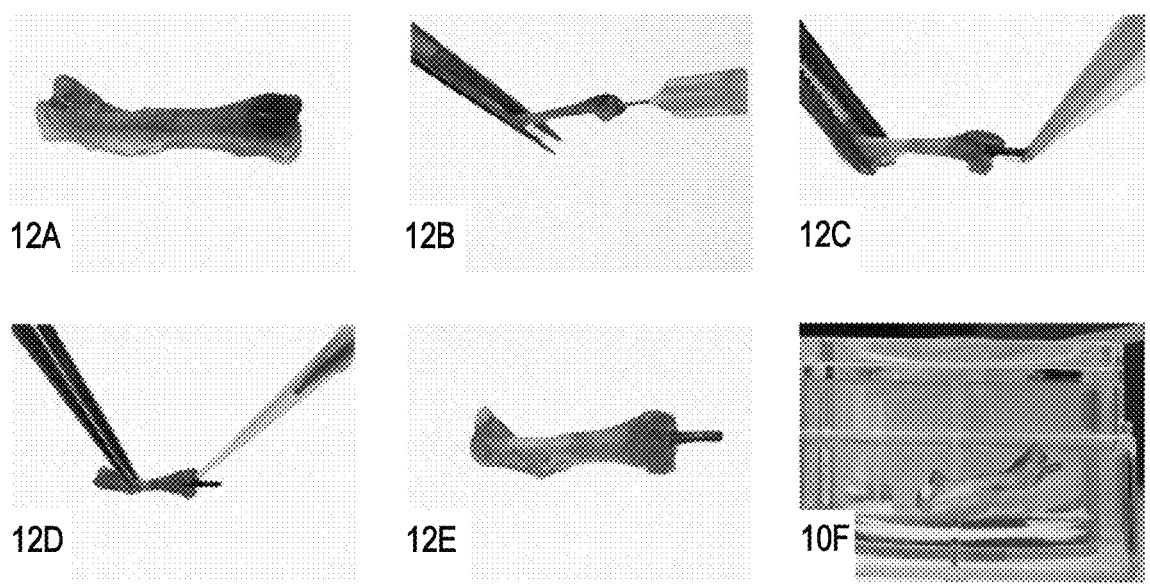

In order to avoid direct contact between SNPSAs and cell culture medium, the distal femur with a protruding SNPSA was angled superiorly, and the proximal femur was soaked in culture medium (FIG. 12).

After 18 h of incubation at 37° C., 5% CO2, and 95% humidity, SNPSAs were removed from the intramedullary canal and incubated in 1 ml nutrient PBS (1×PBS with 0.25% glucose, 0.2% ammonium sulfate, and 1% sterile bacterial growth broth) for 18 h. 100 µl of released bacteria was transferred into a 96-well microplate and amplified by adding 100 µl fresh bacterial culture broth for another 40 h.

Proliferation of the released daughter cells was monitored at a wavelength of 595 nm using an Infinite f200 microplate reader (Tecan, Durham, N.C.) to generate a time-proliferation curve for each well of the microplate, as previously described.

In this assay, lagging or absent bacterial growth was diagnostic of partial or complete inhibition by the SNPSA, such that only a few or no daughter cells were able to colonize the substrate.

Example 5

Protein Adsorption In Vitro

SNPSA discs were incubated at 37° C. for 20 h with 500 µl α-MEM containing 10% FBS and either 0.1 mg/ml bovine serum albumin (BSA; Fisher Scientific) or 0.1 mg/ml BMP-2 (Medtronic, Minneapolis, Minn.). To harvest all adsorbed proteins, SNPSAs were then incubated in 10 mM TRIS (Fisher Scientific) and 1 mM EDTA (Fisher Scientific) for 6 h at 4° C. Protein concentration was measured using the Bio-Rad® Protein Assay (Bio-Rad, Hercules, Calif.) with the Tecan Infinite f200 microplate reader.

Example 6

In Vitro Osteoinductivity $2 \times 10^3$ pre-osteoblastic MC3T3-E1 murine cells (passage 18, subclone 4, ATCC CRL-2593) were seeded on SNPSA discs with 500 µl osteogenic medium (α-MEM supplied with 10% FBS, 1% HT supplement, 100 unit/ml penicillin, 100 µg/ml streptomycin, 50 µg/ml ascorbic acid and 100 mM β-glycerophosphate) in 24-well plates at 37° C., 5% $CO_2$, and 95% humidity. All media for cell culture were purchased from Invitrogen. Cell proliferation was estimated using the Vybrand® MTT Cell Proliferation Assay Kit (Invitrogen). ALP activity and degree of mineralization (assessed by Alizarin Red staining) were used to quantify the effect of silver nanoparticle/PLGA-coated stainless steel alloy on osteoblastic differentiation.

Example 7

Rat Fc Model

All surgical procedures were approved by the UCLA Office of Animal Research Oversight (protocol #2008-073). Using aseptic technique, a 25-30 mm longitudinal incision was made over the anterolateral aspect of the left femur of 12-week old male Sprague-Dawley (SD) rats. The femoral shaft was then exposed by separating the vastus lateralis and biceps femoris muscles. Using a micro-driver (Stryker, Kalamazoo, Mich.), four canals were drilled on each femur with 2-mm interface. SNPSA K-wires were implanted into each predrilled canal. For bacterial inoculation, $10^3$ CFU S. aureus Mu50 or P. aeruginosa PAO-1 in 10 µl PBS ($10^5$ CFU/ml) was pipetted into the canal before implantation. After inoculation, the overlying muscle and fascia were closed with 4-0 Vicryl absorbable suture to secure the implant in place. Following surgery, the animals were housed in separate cages and allowed to eat and drink ad libitum. Weight bearing was started immediately postoperatively, and the animals were monitored daily. Buprenorphine was administered for 2 days as an analgesic, but no antibiotic was administered.

Example 8

At 2, 4, 6, and 8 weeks post-surgery, high-resolution lateral radiographs were obtained while the animals were under isoflurane anesthesia. The animals were euthanized at 8 weeks post-implantation. Operated femurs were dissected, harvested, and fixed in 10% buffered formalin (Fisher Scientific). Following 48 h fixation, samples were scanned using high-resolution micro-computed tomography (microCT; Skyscan 1172, Skyscan, Belgium) at an image resolution of 20.0 µm (55 kVp and 181 µA radiation source with 0.5 mm aluminum filter). 2D and 3D high-resolution reconstruction images were acquired using the software provided by the manufacturer.

Example 9

Histological and Immunohistochemical (IHC) Evaluation

After 3D microCT scanning, the specimen was decalcified using 10% EDTA solution (pH 7.4, Fisher Scientific, Hampton, N.H.) for 21 days, washed with running tap water for 3-4 h, transferred to a 75% ethanol solution, and embedded in paraffin. 5-µm sagittal sections of each specimen were collected. Hematoxylin and eosin (H&E) staining and Masson's Trichrome staining were used to assess morphology. Taylor-modified Brown and Brenn Gram staining and Giemsa staining were used to assess bacterial contamination and inflammation, respectively. In addition, IHC staining for osteocalcin (OCN, Santa Cruz Biotechnology, Santa Cruz, Calif.) was applied to evaluate new bone generation.

Example 10

Statistical Analysis

All results are presented as mean±standard error of mean (s.e.m.). Statistical significance was computed using one-way ANOVA and independent-samples t-test (Origin 8; OriginLab Corp., Northampton, Mass.). $P<0.05$ was considered statistically significant. All statistical analyses in this manuscript were conducted per consultation with the UCLA Statistical Biomathematical Consulting Clinic (SBCC).

Example 11

Characterization of SNPSAs

SNPSA was produced by repeated incubations of 316L steel alloy in silver nanoparticle/PLGA-chloroform solution. A uniform layer of silver nanoparticle/PLGA composite was observed on the surface of the stainless steel alloy (FIGS. 1a and 2). In addition, aggregates of silver nanoparticles sintered together were not observed in silver nanoparticle/PLGA layers containing up to 2.0% silver nanoparticles (FIGS. 1a and 2).

SEM revealed that the thickness of silver nanoparticle/PLGA layer coated on K-wires was 43.36±0.08 µm (FIG. 1b; N=8). Densities of coated silver nanoparticle/PLGA composite were 0.263 g/cm$^3$, 0.278 g/cm$^3$, and 0.293 g/cm$^3$, for 0%, 1%, and 2% silver nanoparticles, respectively; thus, the overall doses of silver nanoparticle-coated on the K-wires were: $\pi \times [(\text{Thickness}_{silvernanoparticle/PLGA} + \text{Radius}_{Alloy})^2 - \text{Radius}_{Alloy}^2] \times \text{Density}_{silvernanoparticle/PLGA} \times \text{Proportion}_{silvernanoparticle}$=0 µg/cm, 2.44 µg/cm, and 5.14 µg/cm for 0%, 1%, and 2% SNPSA, respectively.

Example 12

Contact Angle and Surface Free Energy of SNPSAs

The contact angles on the SNPSAs obtained before and after incubation in osteogenic medium are summarized in Table 2. Notably, the values of contact angle for the liquids applied on 0%-SNPSA differed only slightly before and after incubation in osteogenic medium. In contrast, the values of contact angle for the liquids applied on 1%- and 2%-SNPSAs dramatically changed after the incubation (Table 3).

TABLE 3

Contact angles of the standard liquids on the SNPSAs.

| Silver proportion (%) | Water | Glycerol | Formamide | Ethylene glycol |
|---|---|---|---|---|
| Contact angle θ (°) before incubation* | | | | |
| 0% | 48.6 ± 0.1 | 51.9 ± 0.1 | 45.1 ± 0.2 | 43.0 ± 0.2 |
| 1% | 49.7 ± 0.1 | 54.0 ± 0.2 | 48.3 ± 0.2 | 44.1 ± 0.1 |
| 2% | 50.3 ± 0.1 | 57.3 ± 0.2 | 50.1 ± 0.2 | 48.7 ± 0.2 |
| Contact angle θ (°) after incubation in osteogenic medium*[#] | | | | |
| 0% | 47.0 ± 0.2 | 52.5 ± 0.1 | 40.6 ± 0.1 | 43.8 ± 0.2 |
| 1% | 36.1 ± 0.2 | 51.4 ± 0.1 | 37.4 ± 0.2 | 37.4 ± 0.1 |
| 2% | 27.9 ± 0.2 | 50.1 ± 0.1 | 35.4 ± 0.2 | 29.2 ± 0.2 |

*Data were shown as mean ± SEM (N = 6)
[#]SNPSAs were incubated in osteogenic medium for 9 days.

Figure 3:
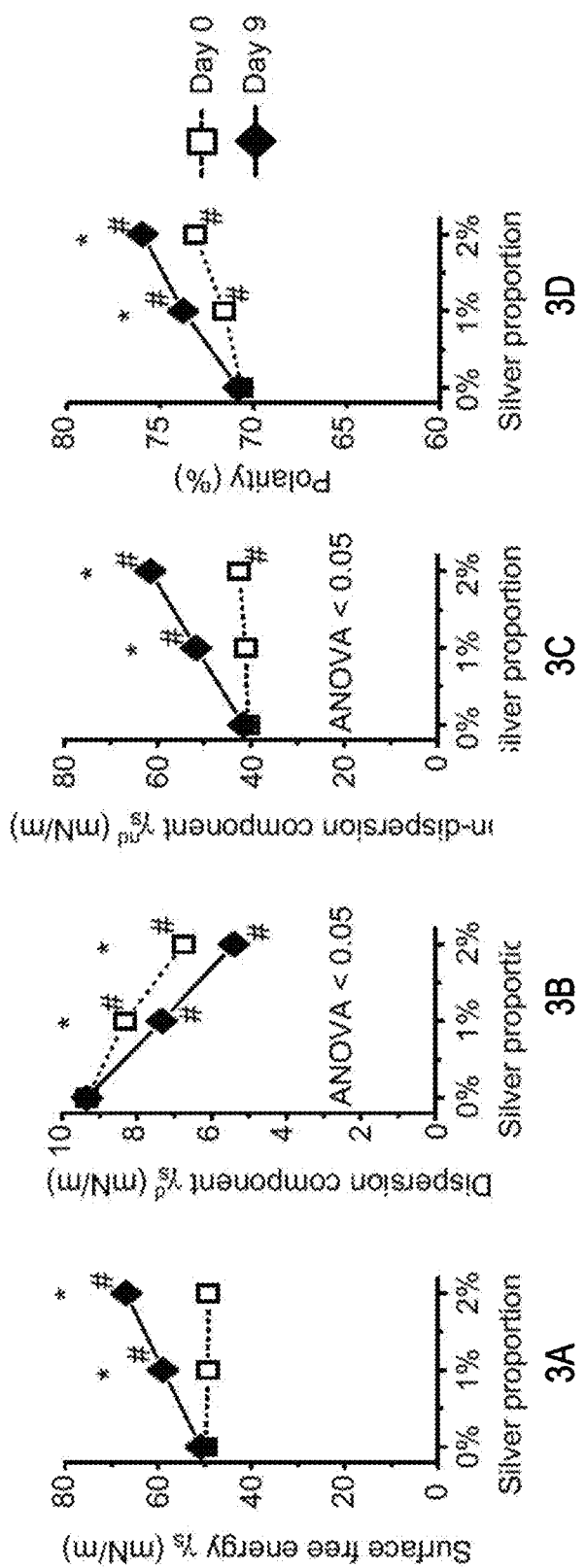

Using the contact angle values and Eq. (1), surface free energy and its dispersion and non-dispersion components of SNPSAs were calculated (FIG. 3). The presence of silver nanoparticles had minimal effect on the surface free energy of SNPSAs before incubation in osteogenic medium; however, the surface free energy of SNPSAs increased significantly as a function of silver proportion after 9 days of incubation in osteogenic medium (FIG. 3a).

Interestingly, the dispersion component $\gamma_s^d$ decreased with increasing silver proportion (FIG. 3b) but remained quite small compared to the non-dispersion component $\gamma_s^{nd}$ (FIG. 3c); moreover, incubation in osteogenic medium further decreased yd (FIG. 3b). In contrast, the non-dispersion (or 'polar') component $\gamma_s^{nd}$ increased with silver proportion, and incubation in osteogenic medium resulted in more dramatically increased $\gamma_s^{nd}$ as a function of silver proportion (FIG. 3c).

As a result, the polarity of SNPSAs, defined as $$\frac{\gamma_s^{nd}}{\gamma_s} \times 100\%,$$

increased with silver proportion (FIG. 3d). It is noteworthy that incubation in osteogenic medium did not influence the polarity of PLGA-coated alloy without silver nanoparticles (0%-SNPSA), but the same incubation resulted in significantly increased polarity of both 1%- and 2%-SNPSAs (FIG. 3d).

Example 13

In Vitro Antimicrobial Activity of SNPSAs

Figure 6:
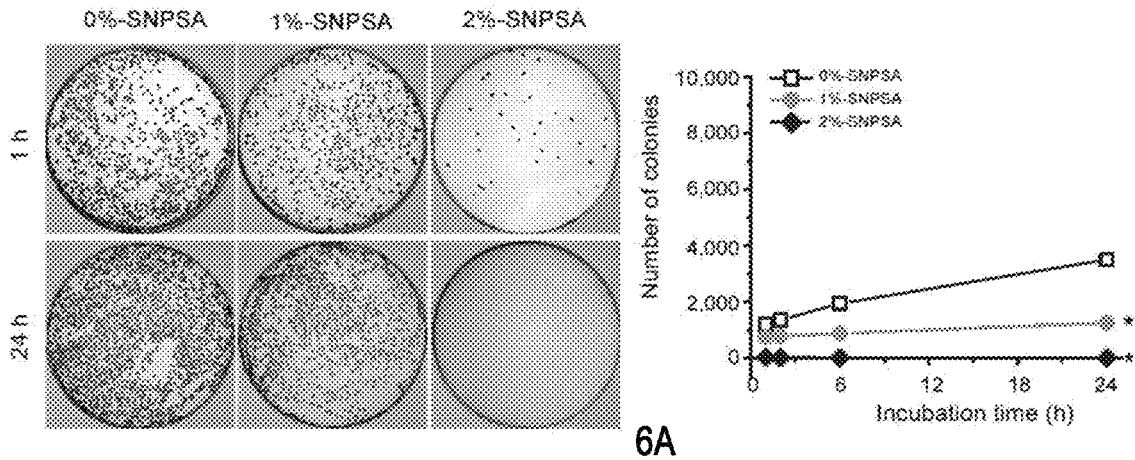
Figure 6:
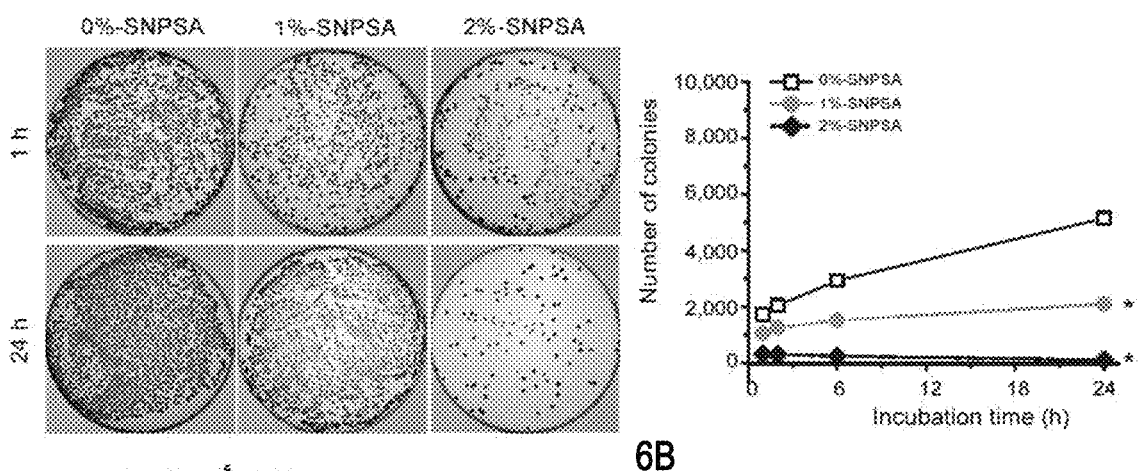
Figure 6:
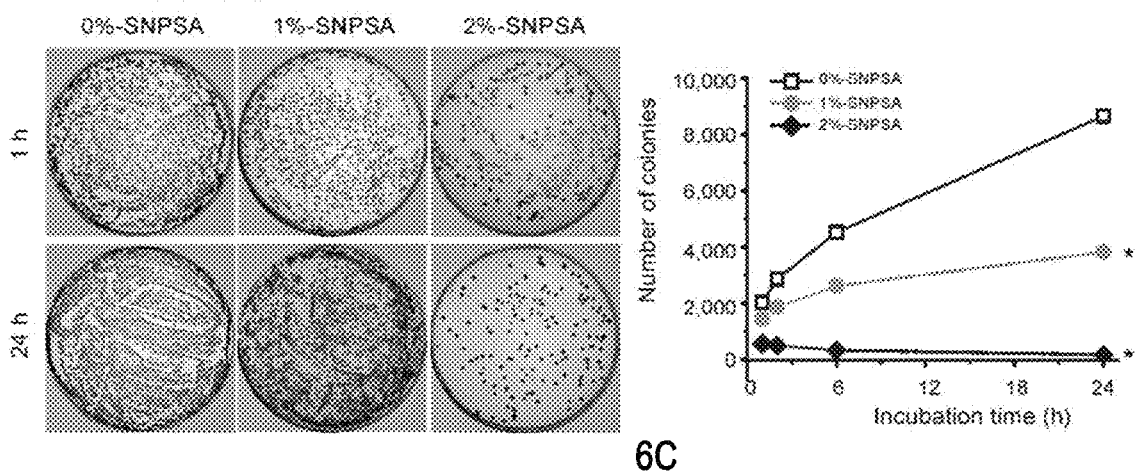

Analysis of bacterial colonization showed that, when compared to 0%-SNPSA, 1%- and 2%-SNPSAs inhibited the initial adherence of S. aureus Mu50 (FIG. 6) and P. aeruginosa PAO-1 (FIG. 7) after 1 h incubation in the bacterial broth in a silver-proportion-dependent manner. Quantification of CFU formation demonstrated that, when 0%-SNPSA was incubated with 10$^3$ CFU S. aureus Mu50, almost all the bacteria initially adhered to the alloy surface within the first hour of incubation, and the number of bacteria markedly increased with incubation time (FIG. 6a).

This result suggested that S. aureus Mu50 proliferated extensively on 0%-SNPSA surface after adherence. 1% silver nanoparticles slightly reduced initial adherence of 10$^3$ CFU S. aureus Mu50 but significantly inhibited its proliferation on the coated alloy (FIG. 6a). Initial adherence of 10$^3$ CFU S. aureus Mu50 to 2%-SNPSA was less than 5% (FIG. 6a). Furthermore, no bacteria survived at an initial inoculum of 10$^3$ CFU after 24 h incubation with 2%-SNPSA (FIG. 6a). In addition, 2%-SNPSA presented similar antibacterial properties against the adherent bacteria from 10$^3$ CFU P. aeruginosa PAO-1 as those from the same initial inoculum of S. aureus (FIG. 7a).

When the initial inocula of both species were increased to 10$^4$ and 10$^5$ CFU, about 2×10$^3$ bacteria initially adhered to the 0%-SNPSA and proliferated during the incubation (FIGS. 6b and 6c, and FIGS. 7b and 7c). In contrast, only about 1×10$^3$ bacteria initially adhered to the 1%-SNPSA, and their extended proliferation was significantly decreased (FIGS. 6b and 6c, and FIGS. 7b and 7c). Remarkably, at the established ceiling of 2% silver, initial bacterial adherence was significantly inhibited (FIGS. 6b and 6c, and FIGS. 7b and 7c). Although 2%-SNPSA was not enough to kill all adherent bacteria from 10$^4$ or 10$^5$ CFU inoculum within 24 h, less than 1% of adherent bacteria survived (FIGS. 6b and 6c, and FIGS. 7b and 7c).

Example 14

Ex Vivo Antimicrobial Activity of SNPSAs

In order to further evaluate the effect of silver nanoparticle/PLGA coating on preventing bacterial adherence and biofilm formation on the surface of implants, an ex vivo contamination model (FIG. 12) was employed with a previously reported microplate proliferation assay. The ex vivo model was used to observe the antibacterial activity of SNPSA independently of host immunological responses and to compare its antibacterial activity with that observed in the in vivo contamination model of rat FCs. SEM revealed that placing the SNPSA K-wires into the pre-reamed intramedullary canal did not damage the coating significantly (FIG. 1b).

Figure 9:
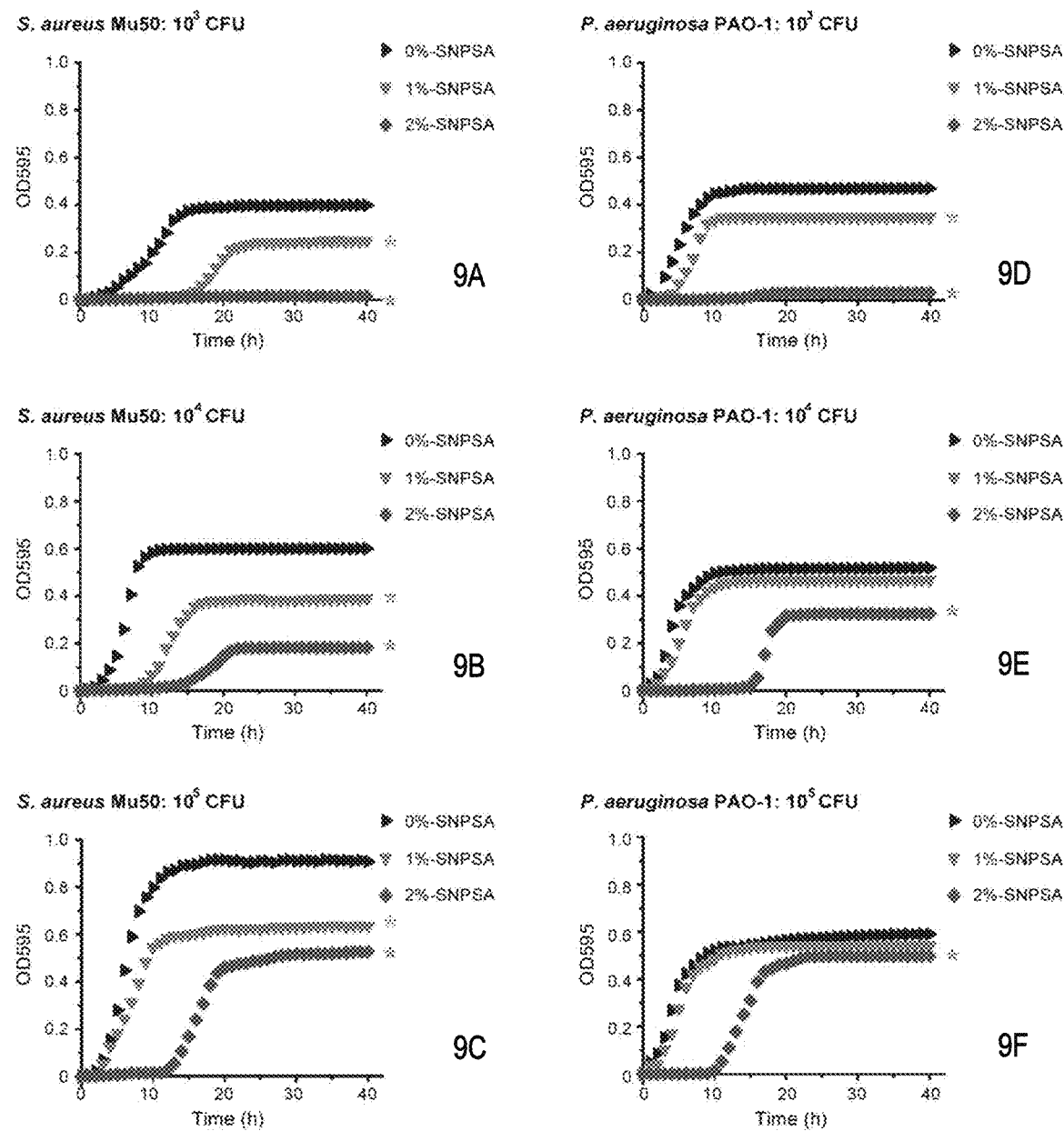
Figure 10:
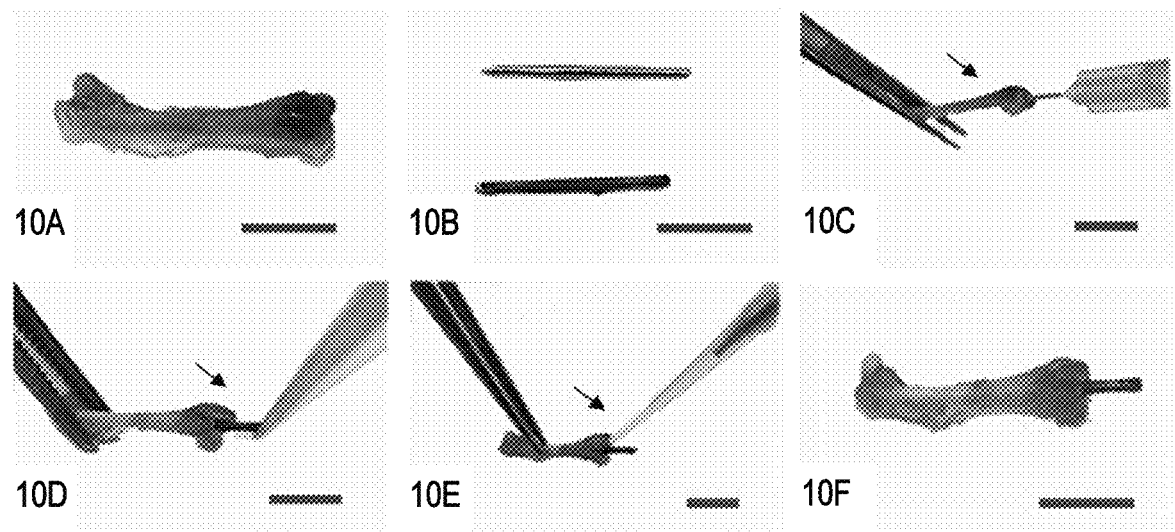

Control 0%-SNPSA did not inhibit ex vivo bacterial adherence or proliferation, while silver-proportion-dependent antimicrobial activity was observed in 1%- and 2%-SNPSAs (FIG. 9). 1%-SNPSAs significantly inhibited 10$^3$-10$^5$ CFU S. aureus Mu50 ex vivo growth on the coated alloy surface (FIGS. 9a-9c). However, the inhibition against 10$^3$ CFU P. aeruginosa PAO-1 growth by 1%-SNPSA was minimal (FIG. 9d), and no considerable effects of 1% silver nanoparticle against $10^4$ or $10^5$ CFU P. aeruginosa PAO-1 were observed ex vivo (FIGS. 9e, and 9f). Higher silver proportion at 2% silver nanoparticle was more effective against ex vivo growth of $10^4$ or $10^5$ CFU S. aureus Mu50 (FIGS. 9b and 9c) and P. aeruginosa PAO-1 (FIGS. 9e and 9f), respectively. Furthermore, ex vivo growth of 103 CFU S. aureus Mu50 and P. aeruginosa PAO-1 was completely inhibited by 2%-SNPSA (FIGS. 9a and 9d).

Example 15

Protein Adsorption on SNPSAs In Vitro

Figure 4:
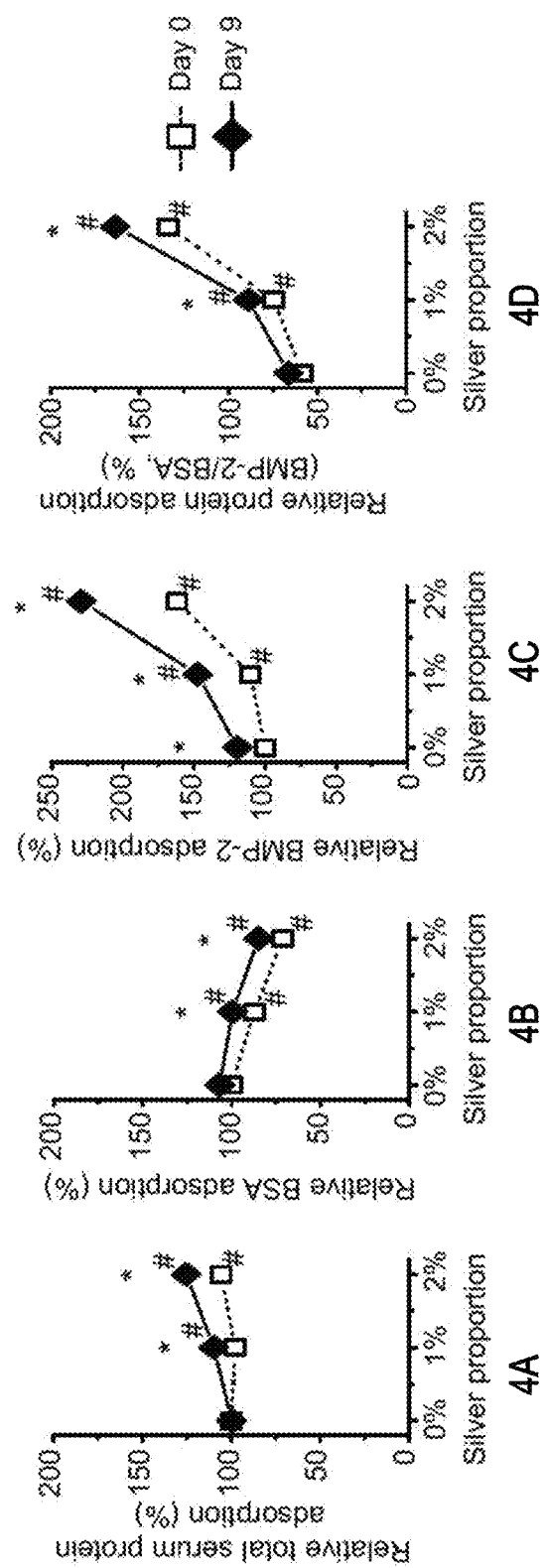

Protein adsorption was detected on SNPSAs (FIG. 4). Clearly, a positive correlation between surface free energy and the total serum protein adsorption was observed: the higher the surface free energy, the more protein adsorbed onto the SNPSA surfaces and vice versa (FIGS. 3 and 4a). Surprisingly, SNPSAs exhibited selective protein adsorption in a silver-proportion-dependent manner: as silver proportion increased in SNPSAs, adsorption of the control protein BSA decreased (FIG. 4b) while that of the osteoinductive growth factor BMP-2 increased (FIG. 4c). This selectivity was more significant after the incubation in osteogenic medium (FIG. 4d).

Example 16

In Vivo Osteogenic Activity of SNPSAs In Vitro

The MTT assay was used to compare mouse MT3T3-E1 pre-osteoblastic cell proliferation on different SNPSAs (FIG. 14a). Generally, silver nanoparticles resulted in increased MC3T3-E1 cell proliferation on SNPSAs in a silver-proportion-dependent manner (FIG. 14a).

Interestingly, along with the culture time, SNPSAs with higher silver proportions promoted cell proliferation more potently (FIG. 14a). For example, cell proliferation on 2%-SNPSA was 1.17, 1.63, and 1.88 times greater than that on control 0%-SNPSA after 3, 6, and 9 days in osteoblastic differentiation medium, respectively. To assay osteoblastic cell function, ALP activity in MC3T3-E1 cells was measured after 9 days in osteoblastic differentiation medium. SNPSAs significantly increased ALP activity of ongrowth cells compared to 0%-silver nanoparticle controls (FIG. 14b).

Furthermore, SNPSAs also significantly promoted ongrowth terminal differentiation of osteoblasts, as indicated by mineralization, during the 21-day culture period (FIG. 14c). Therefore, SNPSAs exhibited osteoinductive properties in a silver-proportion-dependent manner in vitro.

Example 17

Effects of SNPSA Implants in Rat FCs

Figure 15:
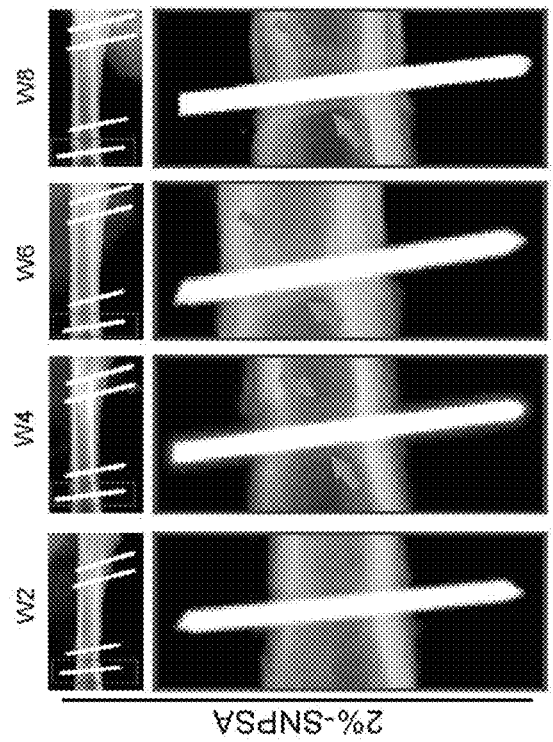
Figure 15:
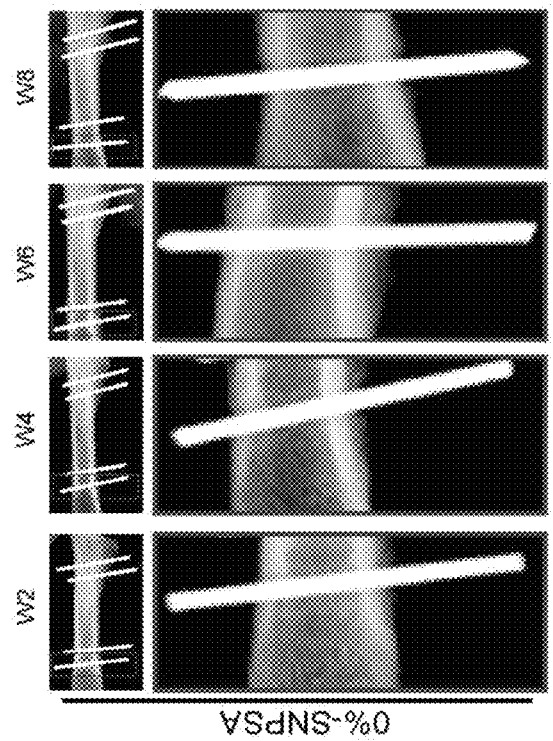
Figure 16:
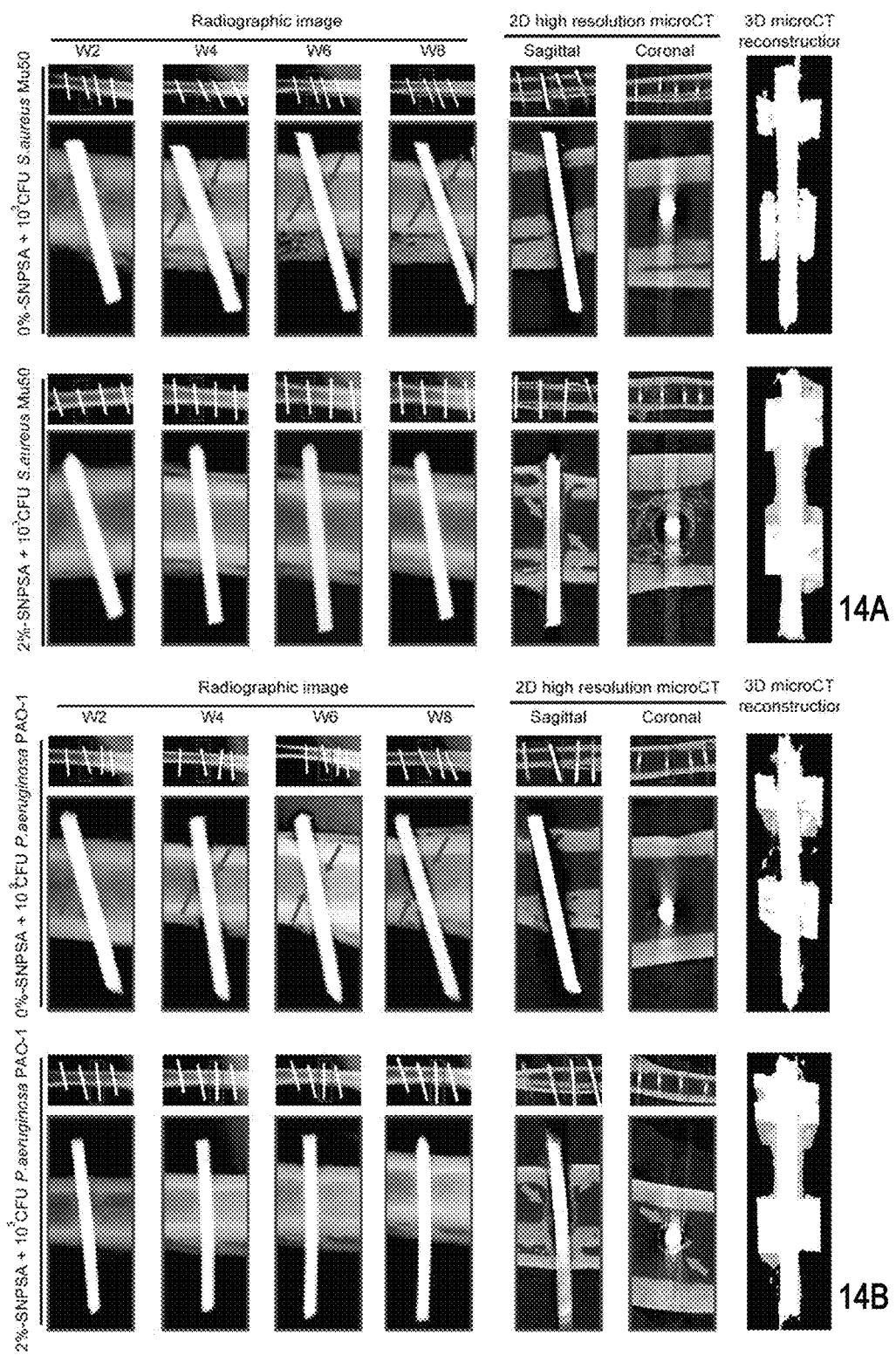
Figure 17:
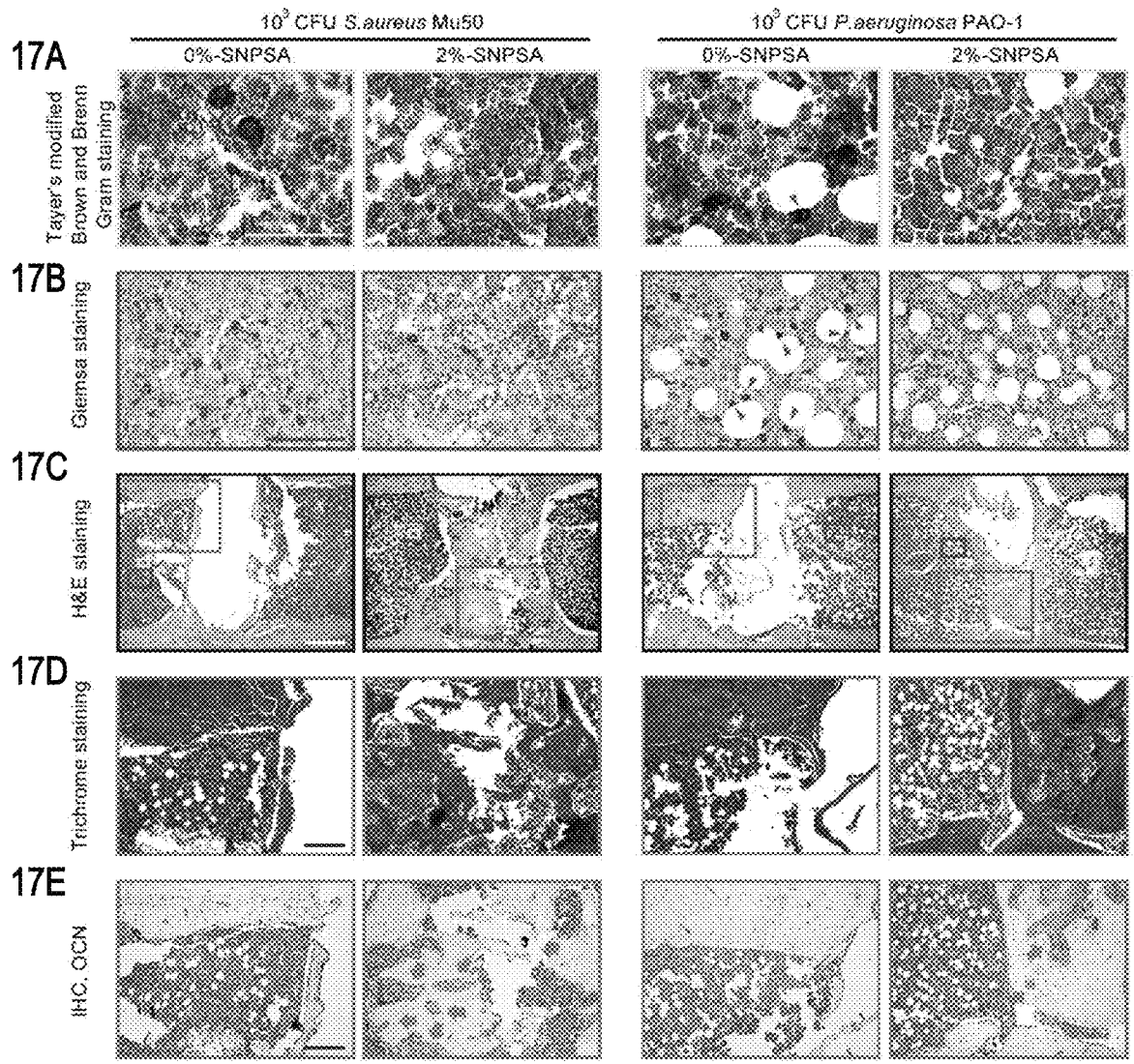

Radiography
No obvious radiographic signs of bone formation were observed in rat FCs implanted with either uncontaminated (FIG. 15) or bacterially contaminated (FIG. 16) 0%-SNPSAs up to 8 weeks post-surgery; instead, radiographic evidence of osseous destruction was detected in the contaminated 0%-SNPSA group (FIG. 16). In contrast, significant bone formation surrounding 2%-SNPSAs implants in rat FCs was observed despite the initial contamination with $10^3$ CFU bacteria (FIGS. 15 and 16). In addition, no osteolysis was observed in the contaminated 2%-SNPSAs group (FIG. 16). Radiographic findings of bone formation surrounding contaminated 2%-SNPSA implants in rat FCs were also confirmed by 3D microCT analysis (FIG. 16).

Histological and IHC Evaluation

Microscopic examination revealed bacterial persistence (FIG. 17a) accompanied by many inflammatory cells (FIG. 17b) in the intramedullary tissues around 0%-SNPSA implants in rat FCs 8 weeks after implantation with $10^3$ CFU initial bacterial inoculum. In contrast, no bacterial survival was evident around 2%-SNPSA implants under the same conditions (FIG. 17a), and inflammatory cell infiltration in the intramedullary tissues around the implants was minimal (FIG. 17b). Thus, 2%-SNPSA implants markedly inhibited bacterial invasion without evoking significant host inflammatory responses in vivo.

Newly formed bone around SNPSA implants was further evaluated by H&E staining, Trichrome staining, and IHC staining with an antibody against OCN, a marker of mature differentiated osteoblasts, at 8 weeks after implantation with $10^3$ CFU initial bacterial inoculum. Only minimal bone formation around the 0%-SNPSA groups was observed (FIGS. 17c and 17d). On the other hand, consistent with radiographic analyses, significant bone formation was detected around 2%-SNPSA implants (FIGS. 17c and 17d), and intense osteocalcin (OCN) staining signified that new bone formation was still active around 2%-SNPSA implants at week 8 after implantation (FIG. 17e). Taken together, 2%-SNPSA implants exhibited significant osteoinductive as well as antibacterial effects in vivo.

Since the first applications of surgically-implanted materials in humans, bacterial infections have represented a common and challenging problem. Bacterial adherence to the foreign implanted materials and subsequent biofilm formation are hallmarks of implant-associated infections. As a result, prevention of bacterial colonization and biofilm formation on implants by administration of prophylactic antibiotics has been extensively studied. Interestingly, most of these studies are focused on preventing S. aureus contamination, as this species is the leading cause of implant-associated infections due to its high affinity to bone, rapid induction of osteonecrosis, and resorption of bone matrix. However, other bacterial species, including P. aeruginosa, S epidermidis, Klebsiella ozaenae, and Escherichia coli, are also commonly involved in implant-associated infections in orthopedic surgery, and some studies have even reported P. aeruginosa as a major isolated organism. Because pathogens involved in implant-associated infections are diverse, and bacteria in biofilms are protected from the host immune responses and antibiotics, the restricted activity of antibiotics against implant infections limits their clinical effectiveness. This is especially the case in infections involving antibiotic-resistant bacterial strains (e.g. MRSA strains), which are increasing in both healthcare and community settings and are becoming a major threat to public health.

Because of its antimicrobial properties, silver has been extensively used in water recycling and sanitization and for treatment of wound infections. Currently, silver is gaining renewed attention as a medical antimicrobial agent due to its broad antibacterial spectrum and the difficulty of developing bacterial resistance to silver. For instance, silver is used to reduce bacterial colonization in a variety of pharmaceutical devices including vascular and urinary catheters, endotracheal tubes, and implantable prostheses. Mechanistically, silver prevents cell division and transcription by binding to and disrupting multiple components of bacterial structure and metabolism, including cellular transport, essential enzyme systems such as the respiratory cytochromes, and synthesis of cell wall components, DNA and RNA; nevertheless, the reservoir form of the active silver form may be diverse. Previously, ionic reservoir forms of silver such as silver nitrate ($AgNO_3$) and silver sulfate ($Ag_2SO_4$) have been used to provide protection against bacterial infections. However, despite its effective short-term antibacterial activity, inadequate local retention and severe cytotoxic effects of ionic silver ($Ag^+$) have made it undesirable for continually preventing bacterial colonization on the implants. Recent reports have shown that that 20-25 nm silver nanoparticles effectively inhibit microorganisms without causing significant cytotoxicity, and that 10-20 nm silver nanoparticles are nontoxic in mice and guinea pigs when administered by the oral, ocular and dermal routes. These findings suggest silver nanoparticles of the size evaluated in the present study are appropriate for therapeutic application from a safety standpoint.

In addition, the preparation and stabilization of silver nanoparticles remain challenging due to their tendency to aggregate. Several polymers have been used to stabilize silver nanoparticles, including polyethyleneimine, polyallylamine, poly(vinyl-pyrrolidone), and chitosan. The nucleophilic character of these polymers, albeit minor, is sufficient for them to bind to the metal particles by donating electrons.

The US Food and Drug Administration (FDA)-approved, biodegradable and biocompatible polymer PLGA has been chosen in this study because its hydrolysable ester bonds are subject to nucleophilic interactions with incorporated components such as silver particles. Another advantage of PLGA is that it could be applied onto implants using solvent casting techniques, which allow coating of alloys and even plastic surfaces with polished, irregular or porous materials.

Figure 2C:
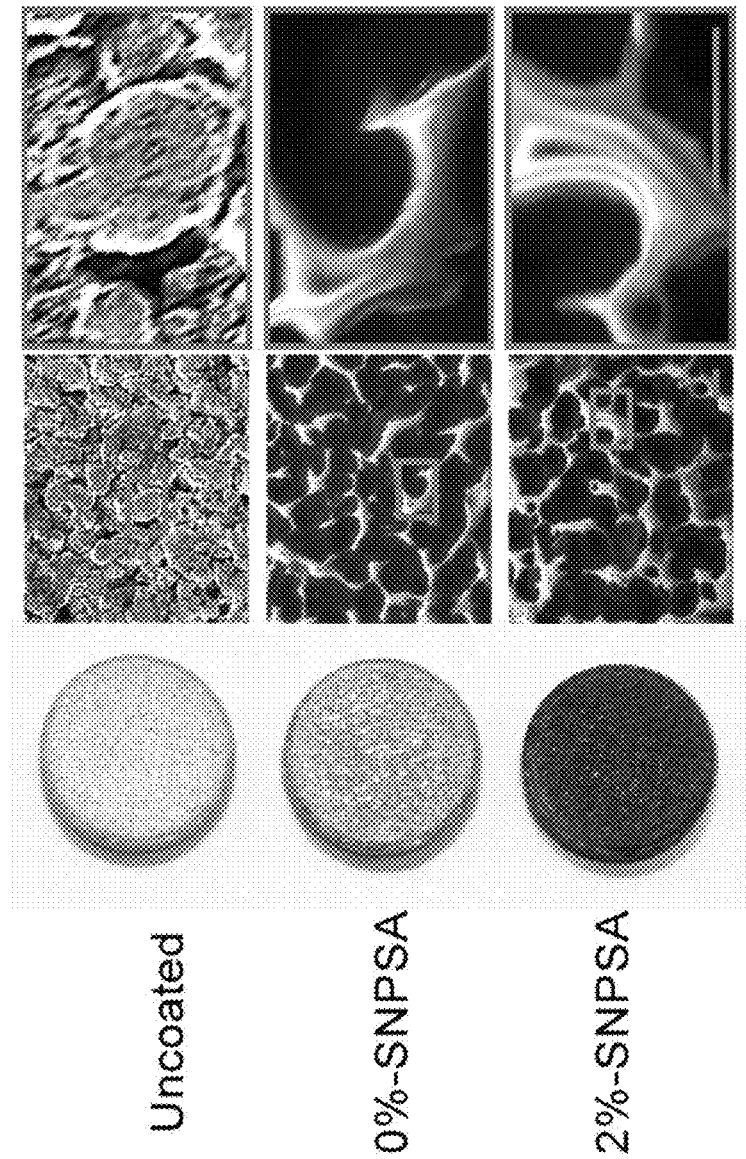

For instance, up to 2% silver nanoparticles were coated onto 316L stainless steel alloy within PLGA without aggregation (FIG. 1 and FIG. 2c). In addition, PLGA degradation is based on hydrolytic splitting of the polymer backbone into oligomers and release of lactic acid and glycolic acid, two byproducts of various metabolic pathways in the body under normal physiological conditions. Thus, a local delivery system that incorporates silver nanoparticles into the polymer coating ensures not only high local concentrations around the implant for long periods but also reduced risks and side effects for the host organism compared to systemic drug application.

Figure 7:
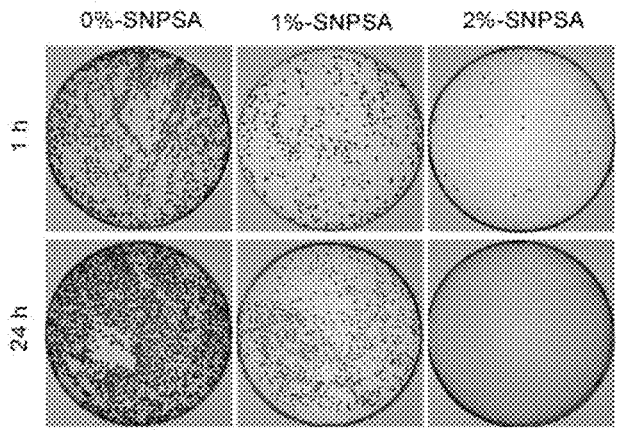
Figure 7:
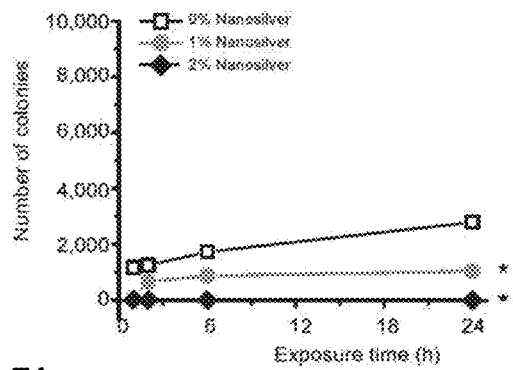
Figure 7:
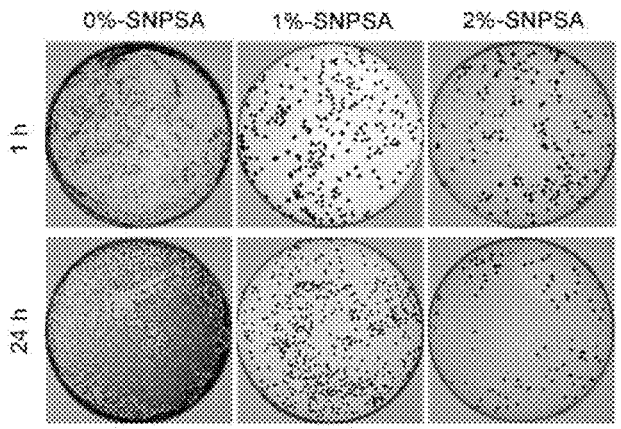
Figure 7:
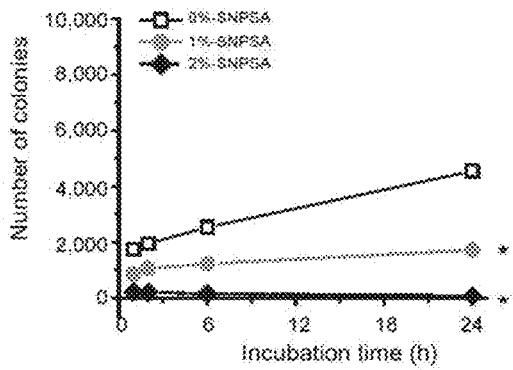
Figure 7:
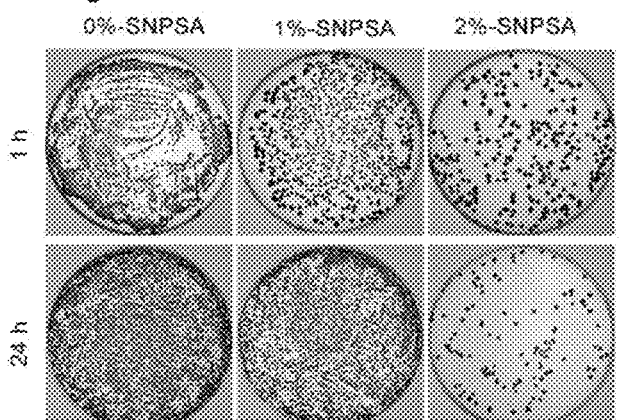
Figure 7:
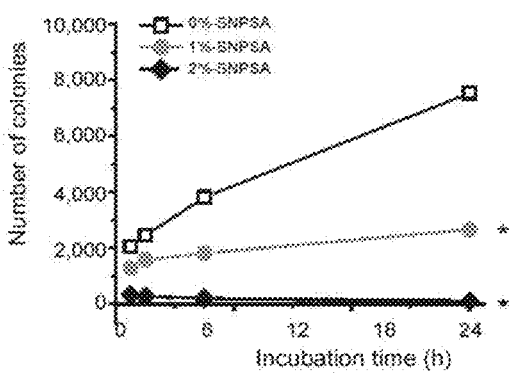
Figure 8:
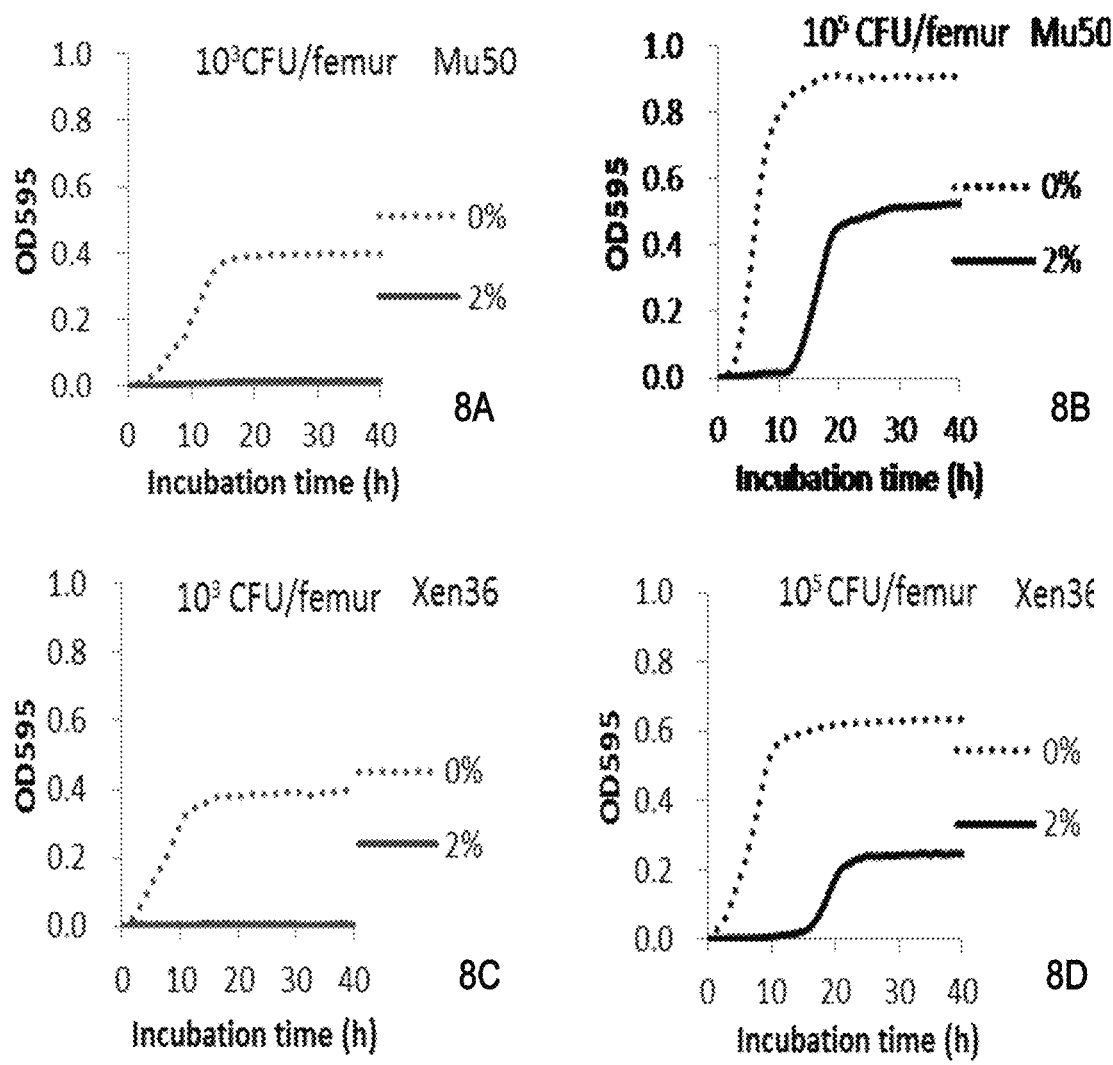

In this study, the results from in vitro and ex vivo assays demonstrated that 2%-silver nanoparticle/PLGA coating effectively prevented bacterial adherence and biofilm formation on the stainless steel alloy implants (FIGS. 6, and 7, and 9). Using a rat FC model, it was found that 2%-SNPSA displayed significant antibacterial activity against contamination with $10^5$ CFU/ml Gram-positive *S. aureus* Mu50 or Gram-negative *P. aeruginosa* PAO-1 (FIGS. 16 and 17), a bacterial burden typical of invasive tissue infection. In addition, by employing BMP-2-coupled silver nanoparticle/PLGA composite grafts, bone formation was successfully regenerated in a 6-mm critical-sized rat FSD grossly infected with $10^9$ CFU/ml vancomycin intermediate *Staphylococcus aureus* (VISA)/MRSA strain Mu50. Collectively, the findings support the application of silver nanoparticle/PLGA composite for localized prophylaxis of implant-associated infections.

Notably, surface free energy of SNPSA, especially its non-dispersion component $\gamma_s^{nd}$ increases with silver proportion after incubation in osteogenic medium (FIG. 4c). Silver nanoparticles in SNPSA may have contributed to the non-dispersion component of surface free energy by progressively releasing cationic silver [$Ag^+$, i.e. ionic silver Ag(I)] and/or exposing partially oxidized silver nanoparticles with $Ag^+$ chemisorbed to the surface of SNPSA during the incubation.

As a result, the non-dispersion component of surface free energy, the total surface free energy, and the polarity are all increased after incubation in osteogenic medium in a silver-proportion-dependent manner (FIG. 3). In turn, the increased surface free energy, especially its non-dispersion component, imparts higher bioactivity and increased total protein adsorption to the material after incubation in osteogenic medium (FIG. 4a). Surprisingly, adsorption of BMP-2 on the SNPSA surface is positively correlated with the non-dispersion component of surface free energy, which increases along with the silver proportion and incubation time in osteogenic medium; conversely, adsorption of BSA decreases slightly with increased silver proportion and is not significantly affected by the incubation (FIG. 4b). This result suggests that SNPSAs may have the ability to adsorb proteins selectively in a silver-proportion-dependent manner, which may explain their markedly osteoinductive activity in vitro (FIG. 14) and in vivo (FIGS. 16 and 17) when BMP-2 is applied. However, further investigation is necessary to determine the mechanism of this selectivity and the effect of incubation.

In summary, we demonstrated that SNPSA successfully inhibited bacterial adherence and biofilm formation in a silver-proportion-dependent manner. Unexpectedly, we also found that SNPSA materials promoted MC3T3-E1 pre-osteoblast proliferation and maturation in vitro. Finally, we used a rat FC model to show that 2%-SNPSA implants have significantly induced bone generation despite bacterial contamination, even at a bacterial inoculum that could cause invasive tissue infection.

From a materials and device development perspective, SNPSA exhibited strong bactericidal and osteoinductive properties that make it a promising pharmaceutical material in orthopedic surgery. The results also indicated that silver nanoparticle/PLGA coating is a practical process that is non-toxic, easy to operate, and free of silver nanoparticle aggregation. In addition, our results revealed that the antibacterial and osteoinductive activities of SNPSA are silver-proportion-dependent, raising the interest in increasing the silver proportion of the coating in future investigations. Further improvement of interfacial adhesion of silver nanoparticle/PLGA coating to different metal surfaces, such as stainless steel alloys, titanium and titanium-based alloys, and cobalt alloys, should be made for clinical application of silver nanoparticle/PLGA-coated implants in orthopedic surgery, especially when permanent implants such as pins for the fixation of bone fracture are indicated.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

Gomez J, Rodriguez M, Banos V, Martinez L, Clayer M A, Ruiz J, et al. Orthopedic implant infection: prognostic factors and influence of long-term antibiotic treatment on evolution. Prospective study, 1992-1999. Enferm Infecc Microbiol Clin. 2003; 21:232-236.

Darouiche R O. Treatment of infections associated with surgical implants. N Engl J. Med. 2004; 350:1422-1429.

Brause B D. Infections with prostheses in bones and joints. In: Mandell G L, Douglas R G, Bennett J E, Dolin R, editors. Principle and practice of infectious diseases. 6th ed. New York: Churchill Livingstong; 2005.

Giavaresi G, Borsari V, Fini M, Giardino R, Sambri V, Gaibani P, et al. Preliminary investigations on a new gentamicin and vancomycin-coated PMMA nail for the treatment of bone and intramedullary infections: An experimental study in the rabbit. J Orthop Res. 2008; 26:785-792.

Shirai T, Tsuchiya H, Shimizu T, Ohtani K, Zen Y, Tomita K. Prevention of pin tract infection with titanium-copper alloys. J Biomed Mater Res B Appl Biomater. 2009; 91:373-380.

Khosravi A D, Ahmadi F, Salmanzadeh S, Dashtbozorg A, Montazeri E A. Study of bacteria isolated from orthopedic implant infections and their antimicrobial susceptibility pattern. Research Journal of Microbiology. 2009; 4:158-163.

Lee J, Singletary R, Schmader K, Anderson D J, Bolognesi M, Kaye K S. Surgical site infection in the elderly following orthopaedic surgery. Risk factors and outcomes. Bone Joint Surg Am. 2006; 88:1705-1712.

Hetrick E M, Schoenfisch M H. Reducing implant-related infections: active release strategies. Chem Soc Rev. 2006; 35:780-789.

Campoccia D, Montanaro L, Arciola C R. The significance of infection related to orthopedic devices and issues of antibiotic resistance. Biomaterials. 2006; 27:2331-2339.

Schierholz J M, Beuth J. Implant infections: a haven for opportunistic bacteria. J Hosp Infect. 2001; 49:87-93.

Sanderson P J. Preventing Infection in Orthopedic Implants. J Antimicrob Chemoth. 1989; 24:277-280.

Taylor G J, Bannister G C, Calder S. Perioperative wound infection in elective orthopaedic surgery. J Hosp Infect. 1990; 16:241-247.

Koort J K, Makinen T J, Suokas E, Veiranto M, Jalava J, Knuuti J, et al. Efficacy of ciprofloxacin-releasing bioabsorbable osteoconductive bone defect filler for treatment of experimental osteomyelitis due to *Staphylococcus aureus*. Antimicrob Agents Chemother. 2005; 49:1502-1508.

Toma M B, Smith K M, Martin C A, Rapp R P. Pharmacokinetic considerations in the treatment of methicillin-resistant *Staphylococcus aureus* osteomyelitis. Orthopedics. 2006; 29:497-501.

Winkler H, Kaudela K, Stoiber A, Menschik F. Bone grafts impregnated with antibiotics as a tool for treating infected implants in orthopedic surgery—one stage revision results. Cell Tissue Bank. 2006; 7:319-323.

Allende C, Mangupli M, Bagliardelli J, Diaz P, Allende B T. Infected nonunions of long bones of the upper extremity: staged reconstruction using polymethylmethacrylate and bone graft impregnated with antibiotics. Chir Organi Mov. 2009; 93:137-142.

Habash M, Reid G. Microbial biofilms: their development and significance for medical device-related infections. J Clin Pharmacol. 1999; 39:887-898.

Jansen B, Peters G. Foreign body associated infection. J Antimicrob Chemother. 1993; 32 Suppl A:69-75.

Costerton J W. Overview of microbial biofilms. J Ind Microbiol. 1995; 15:137-140.

Costerton J W, Lewandowski Z, Caldwell D E, Korber D R, Lappin-Scott H M. Microbial biofilms. Annu Rev Microbiol. 1995; 49:711-745.

Fitzgerald R H, Jr. Experimental osteomyelitis: description of a canine model and the role of depot administration of antibiotics in the prevention and treatment of sepsis. J Bone Joint Surg Am. 1983; 65:371-380.

Petty W, Spanier S, Shuster J J. Prevention of infection after total joint replacement. Experiments with a canine model. J Bone Joint Surg Am. 1988; 70:536-539.

Sarda L, Saleh-Mghir A, Peker C, Meulemans A, Cremieux A C, Le Guludec D. Evaluation of (99m)Tc-ciprofloxacin scintigraphy in a rabbit model of *Staphylococcus aureus* prosthetic joint infection. J Nucl Med. 2002; 43:239-245.

Lucke M, Schmidmaier G, Sadoni S, Wildemann B, Schiller R, Haas N P, et al. Gentamicin coating of metallic implants reduces implant-related osteomyelitis in rats. Bone. 2003; 32:521-531.

Alt V, Bitschnau A, Osterling J, Sewing A, Meyer C, Kraus R, et al. The effects of combined gentamicin-hydroxyapatite coating for cementless joint prostheses on the reduction of infection rates in a rabbit infection prophylaxis model. Biomaterials. 2006; 27:4627-4634.

Antoci V, Jr., Adams C S, Hickok N J, Shapiro I M, Parvizi J. Vancomycin bound to Ti rods reduces periprosthetic infection: preliminary study. Clin Orthop Relat Res. 2007; 461:88-95.

Antoci V, Jr., King S B, Jose B, Parvizi J, Zeiger A R, Wickstrom E, et al. Vancomycin covalently bonded to titanium alloy prevents bacterial colonization. J Orthop Res. 2007; 25:858-866.

Darouiche R O, Mansouri M D, Zakarevicz D, Alsharif A, Landon G C. In vivo efficacy of antimicrobial-coated devices. J Bone Joint Surg Am. 2007; 89:792-797.

Bernthal N M, Stavrakis A I, Billi F, Cho J S, Kremen T J, Simon S I, et al. A mouse model of post-arthroplasty *Staphylococcus aureus* joint infection to evaluate in vivo the efficacy of antimicrobial implant coatings. PLoS One. 2010; 5:e12580.

van de Belt H, Neut D, Schenk W, van Horn J R, van der Mei H C, Busscher H J. Infection of orthopedic implants and the use of antibiotic-loaded bone cements. A review. Acta Orthop Scand. 2001; 72:557-571.

Bouza E, Munoz P. Micro-organisms responsible for osteoarticular infections. Bailliere's best practice & research Clinical rheumatology. 1999; 13:21-35.

Moojen D J, Spijkers S N, Schot C S, Nijhof M W, Vogely H C, Fleer A, et al. Identification of orthopaedic infections using broad-range polymerase chain reaction and reverse line blot hybridization. J Bone Joint Surg Am. 2007; 89:1298-1305.

Ovington L G. The truth about silver. Ostomy Wound Manage. 2004; 50:1S-10S.

Kilgus D J, Howe D J, Strang A. Results of periprosthetic hip and knee infections caused by resistant bacteria. Clin Orthop Relat Res. 2002:116-124.

Hirakawa K, Stulberg B N, Wilde A H, Bauer T W, Secic M. Results of 2-stage reimplantation for infected total knee arthroplasty. J. Arthroplasty. 1998; 13:22-28.

James P J, Butcher I A, Gardner E R, Hamblen D L. Methicillin-resistant *Staphylococcus epidermidis* in infection of hip arthroplasties. J Bone Joint Surg Br. 1994; 76:725-727.

Schreurs W J, Rosenberg H. Effect of silver ions on transport and retention of phosphate by *Escherichia coli*. J. Bacteriol. 1982; 152:7-13.

Seymour C. Audit of catheter-associated UTI using silver alloy-coated Foley catheters. Br J. Nurs. 2006; 15:598-603.

Silver S, Phung le T, Silver G. Silver as biocides in burn and wound dressings and bacterial resistance to silver compounds. J Ind Microbiol Biotechnol. 2006; 33:627-634.

Alt V, Bechert T, Steinrucke P, Wagener M, Seidel P, Dingeldein E, et al. An in vitro assessment of the antibacterial properties and cytotoxicity of nanoparticulate silver bone cement. Biomaterials. 2004; 25:4383-4391.

Leaper D J. Silver dressings: their role in wound management. Int Wound J. 2006; 3:282-294.

Zheng Z, Yin W, Zara J N, Li W, Kwak J, Mamidi R, et al. The use of BMP-2 coupled-Nanosilver-PLGA composite grafts to induce bone repair in grossly infected segmental defects. Biomaterials. 2010; 31:9293-9300.

Webster D A, Spadaro J A, Becker R O, Kramer S. Silver anode treatment of chronic osteomyelitis. Clin Orthop RelatRes. 1981:105-114.

Tamura K. Some effects of weak direct current and silver ions on experimental osteomyelitis and their clinical application. Nihon Seikeigeka Gakkai Zasshi. 1983; 57:187-197.

Nand S, Sengar G K, Jain V K, Gupta T D. Dual use of silver for management of chronic bone infections and infected non-unions. J Indian Med. Assoc. 1996; 94:91-95.

Lok C N, Ho C M, Chen R, He Q Y, Yu W Y, Sun H, et al. Silver nanoparticles: partial oxidation and antibacterial activities. J Biol Inorg Chem. 2007; 12:527-534.

Martinez-Castanon G A, Nino-Martinez N, Martinez-Gutierrez F, Martinez-Mendoza J R, Ruiz F. Synthesis and antibacterial activity of silver nanoparticles with different sizes. J Nanopart Res. 2008; 10:1343-1348.

Lee M, Li W, Siu R K, Whang J, Zhang X, Soo C, et al. Biomimetic apatite-coated alginate/chitosan microparticles as osteogenic protein carriers. Biomaterials. 2009; 30:6094-6101.

Vakula V L, Pritykin L M. Polymer adhesion, basic physiochemical principles. New York: Ellis Horwood; 1991.

Persin Z, Stana-Kleinschek K, Sfiligoj-Smole M, Kreze T, Ribitsch V. Determining the surface free energy of cellulose materials with the powder contact angle method. Text Res J. 2004; 74:55-62.

Zheng Z, Bei F F, Tian H L, Chen G Q. Effects of crystallization of polyhydroxyalkanoate blend on surface physicochemical properties and interactions with rabbit articular cartilage chondrocytes. Biomaterials. 2005; 26:3537-3548.

Good R J. Contact-Angle, Wetting, and Adhesion—a Critical-Review. J Adhes Sci Technol. 1992; 6:1269-1302.

Holloway B W. Genetic recombination in *Pseudomonas aeruginosa*. J Gen Microbiol. 1955; 13:572-581.

Shan Z, Xu H, Shi X, Yu Y, Yao H, Zhang X, et al. Identification of two new genes involved in twitching motility in *Pseudomonas aeruginosa*. Microbiology. 2004; 150:2653-2661.

Chai H, Guo L, Wang X, Fu Y, Guan J, Tan L, et al. Antibacterial effect of 317L stainless steel contained copper in prevention of implant-related infection in vitro and in vivo. J Mater Sci Mater Med. 2011.

De Bartolo L, Morelli S, Bader A, Drioli E. Evaluation of cell behaviour related to physico-chemical properties of polymeric membranes to be used in bioartificial organs. Biomaterials. 2002; 23:2485-2497.

Alers J C, Krijtenburg P J, Vissers K J, van Dekken H. Effect of bone decalcification procedures on DNA in situ hybridization and comparative genomic hybridization. EDTA is highly preferable to a routinely used acid decalcifier. The journal of histochemistry and cytochemistry: official journal of the Histochemistry Society. 1999; 47:703-710.

Taylor R D. Modification of the Brown and Brenn gram stain for the differential staining of gram-positive and gram-negative bacteria in tissue sections. Am J Clin Pathol. 1966; 46:472-474.

Gristina A G. Biomaterial-centered infection: microbial adhesion versus tissue integration. Science. 1987; 237: 1588-1595.

Gristina A G. Implant failure and the immuno-incompetent fibro-inflammatory zone. Clin Orthop Relat Res. 1994: 106-118.

Pribaz J R, Bernthal N M, Billi F, Cho J S, Ramos R I, Guo Y, et al. Mouse model of chronic post-arthroplasty infection: noninvasive in vivo bioluminescence imaging to monitor bacterial burden for long-term study. J Orthop Res. 2012; 30:335-340.

Eron L J. Prevention of infection following orthopedic surgery. Antibiot Chemother. 1985; 33:140-164.

Littlewood-Evans A J, Hattenberger M R, Luscher C, Pataki A, Zak O, OReilly T. Local expression of tumor necrosis factor alpha in an experimental model of acute osteomyelitis in rats. Infect Immun. 1997; 65:3438-3443.

Barth E, Myrvik Q M, Wagner W, Gristina A G. In vitro and in vivo comparative colonization of *Staphylococcus aureus* and *Staphylococcus epidermidis* on orthopaedic implant materials. Biomaterials. 1989; 10:325-328.

von Eiff C, Proctor R A, Peters G. Coagulase-negative staphylococci. Pathogens have major role in nosocomial infections. Postgrad Med. 2001; 110:63-4, 9-70, 3-6.

Ehrman J D, Bender E T, Stojilovic N, Sullivan T, Ramsier R D, Buczynski B W, et al. Microbial adhesion to zirconium alloys. Colloids Surf B Biointerfaces. 2006; 50:152-159.

Mousa H A. Infection following orthopaedic implants and bone surgery. East Mediterr Health J. 2001; 7:738-743.

Hardes J, Ahrens H, Gebert C, Streitbuerger A, Buerger H, Erren M, et al. Lack of toxicological side-effects in silver-coated megaprostheses in humans. Biomaterials. 2007; 28:2869-2875.

Vik H, Andersen K J, Julshamn K, Todnem K. Neuropathy caused by silver absorption from arthroplasty cement. Lancet. 1985; 1:872.

Sudmann E, Vik H, Rait M, Todnem K, Andersen K J, Julsham K, et al. Systemic and local silver accumulation after total hip replacement using silver-impregnated bone cement. Medical progress through technology. 1994; 20:179-184.

Drewa T, Szmytkowska K, Chaberski M. The short term exposition of AgNO3 on 3T3 mouse fibroblasts cell line. Acta Pol Pharm. 2007; 64:175-178.

Martinez-Gutierrez F, Olive P L, Banuelos A, Orrantia E, Nino N, Sanchez E M, et al. Synthesis, characterization, and evaluation of antimicrobial and cytotoxic effect of silver and titanium nanoparticles. Nanomedicine. 2010; 6:681-688.

Maneewattanapinyo P, Banlunara W, Thammacharoen C, Ekgasit S, Kaewamatawong T. An evaluation of acute toxicity of colloidal silver nanoparticles. The Journal of veterinary medical science/the Japanese Society of Veterinary Science. 2011; 73:1417-1423.

Dai J, Bruening M L. Catalytic nanoparticles formed by reduction of metal ions in multilayered polyelectrolyte films. Nano Letters. 2002; 2:497-501.

Kuo P L, Chen W F. Formation of silver nanoparticles under structured amino groups in pseudo-dendritic poly(allylamine) derivatives. J Phys Chem B. 2003; 107:11267-11272.

Yu H, Xu X Y, Chen X, Lu T, Zhang P, Jing X. Preparation and antibacterial effects of PVA-PVP hydrogels containing silver nanoparticles. J Appl Ploym Sci. 2007; 103: 125-133.

Travan A, Pelillo C, Donati I, Marsich E, Benincasa M, Scarpa T, et al. Non-cytotoxic silver nanoparticle-polysaccharide nanocomposites with antimicrobial activity. Biomacromolecules. 2009; 10:1429-1435.

Henglein A. Physicochemical Properties of Small Metal Particles in Solution—Microelectrode Reactions, Chemisorption, Composite Metal Particles, and the Atom-to-Metal Transition. J Phys Chem-Us. 1993; 97:5457-5471.

Houchin M L, Topp E M. Chemical degradation of peptides and proteins in PLGA: A review of reactions and mechanisms. J Pharm Sci-Us. 2008; 97:2395-1404.

Cowsar D R. Introduction to controlled release. Advances in Experimental Medicine and Biology. 1974; 47:1-13.

Calandra T, Cohen J. The international sepsis forum consensus conference on definitions of infection in the intensive care unit. Critical care medicine. 2005; 33:1538-1548.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accor-

What is claimed is:

1. An implantable device, comprising:
   a plurality of silver nanoparticles as an antimicrobial agent dispersed in a polymeric material forming an antimicrobial polymeric coating on at least a portion of a surface of the implantable device and a bioactive agent for bone formation,
   wherein the polymeric material comprises nucleophilic moieties having nucleophilic characteristics that stabilize the silver nanoparticles and the silver nanoparticles constitute about 0.1%-2% or 5% by weight of the polymeric material,
   wherein the bioactive agent is a protein agent selected from the group consisting of bone morphogenetic protein (BMP), transforming growth factor (TGF) beta-1 TGF-beta-2, TGF-beta-3, BMP-2, BMP-3, BMP-7, and insulin-like growth factor (IGF)-1,
   wherein the implantable device is configured such that when it is placed in an osteogenic medium for incubation, surface free energy of the silver nanoparticles on the implantable device, which comprises a non-dispersion component, a dispersion component, and a polar component, increases along with the non-dispersion component, and
   wherein the non-dispersion component imparts higher bioactivity and total protein adsorption to the polymeric material such that adsorption of the protein agent on the surface is positively correlated with the non-dispersion component of surface free energy, which increases along with percentage of the silver nanoparticles and incubation time in the osteogenic medium.

2. The implantable device of claim 1, wherein the silver nanoparticles are deposited on a portion of a surface of the implantable device.

3. The implantable device of claim 1, wherein the implantable device is selected from the group consisting of an implantable intervertebral device, a cervical fusion device, a scaffold, a fixture, a dental implant, a dental disc, a dental bridge, a retainer clip, a dental screw, a dental housing, a dental bone graft, a dental crown, an orthopedic implant, an intramedullary rod, a temporary pin, a permanent pin, a bone plate, a bone screw, and a combination thereof.

4. The implantable device of claim 1, wherein the polymeric material is selected from the group consisting of a biocompatible polymer, a biodegradable polymer, a bioabsorbable polymer, and a combination thereof.

5. The implantable device of claim 1, wherein the silver nanoparticles constitute about 5% by weight of the polymeric material.

6. The implantable device of claim 1, wherein the silver nanoparticles constitute about 2% by weight of the polymeric material.

7. The implantable device of claim 1, wherein the silver nanoparticles have a mean size of 100 nm or smaller.

8. The implantable device of claim 1, wherein the silver nanoparticles have a mean size of 80 nm or smaller.

9. The implantable device of claim 1, wherein the silver nanoparticles have a mean size of 50 nm or smaller.

10. The implantable device of claim 1, wherein the silver nanoparticles have a mean size of 40 nm or smaller.

11. The implantable device of claim 1, wherein the silver nanoparticles have a mean size of between 20 nm and 40 nm.

12. The implantable device of claim 1, wherein the silver nanoparticles have a mean size of 30 nm or smaller.

13. The implantable device of claim 1, further comprising an additional polymeric coating deposited over the antimicrobial polymeric coating that comprises the silver nanoparticles.

14. The implantable device of claim 2, wherein the bioactive agent is BMP-2.

15. The implantable device of claim 13, wherein the bioactive agent is further included in the additional polymeric coating.

16. The implantable device of claim 15, wherein the bioactive agent is BMP-2.

17. A method of fabricating an implantable device according to claim 1, comprising incorporating a plurality of silver nanoparticles as an antimicrobial agent dispersed in a polymeric material comprising nucleophilic moieties having nucleophilic characteristics that stabilize the silver nanoparticles, wherein the antimicrobial agent is deposited discontinuously over a contact surface of the device.

18. The method of claim 17, comprising: forming a coating of the polymeric material on the implantable device, and subsequently depositing the antimicrobial agent to the implantable device.

19. The method of claim 17, comprising: forming a mixture comprising the antimicrobial agent and the polymeric material, depositing the mixture on the implantable device to form a coating.

20. The method of claim 17, comprising: dispersing the antimicrobial agent in the polymeric material to form a mixture, and using the mixture to form a portion of the implantable device or the entire implantable device.

21. The implantable device according to claim 1, wherein the surface comprises an apatite where the surface is modified with the apatite.

* * * * *